(12) United States Patent
Schaub et al.

(10) Patent No.: US 10,647,651 B2
(45) Date of Patent: May 12, 2020

(54) HYDROFORMYLATION PROCESS FOR PRODUCING 1,6-DISUBSTITUTED HEXANE DERIVATIVES

(71) Applicant: BASF SE, Ludwigshafen am Rhein (DE)

(72) Inventors: Thomas Schaub, Ludwigshafen am Main (DE); Rocco Paciello, Ludwigshafen am Main (DE); Martin Ernst, Ludwigshafen am Main (DE); Jaroslaw Mormul, Mannheim (DE); Peter Hofmann, Heidelberg (DE); Jan Breitenfeld, Niederbipp (CH); Oliver Trapp, Munich (DE)

(73) Assignee: BASF SE (DE)

( * ) Notice: Subject to any disclaimer, the term of this patent is extended or adjusted under 35 U.S.C. 154(b) by 210 days.

(21) Appl. No.: 15/767,393

(22) PCT Filed: Oct. 11, 2016

(86) PCT No.: PCT/EP2016/074347
§ 371 (c)(1),
(2) Date: Apr. 11, 2018

(87) PCT Pub. No.: WO2017/064064
PCT Pub. Date: Apr. 20, 2017

(65) Prior Publication Data
US 2018/0297926 A1    Oct. 18, 2018

(30) Foreign Application Priority Data
Oct. 12, 2015 (EP) .................................... 15189341

(51) Int. Cl.
| | | |
|---|---|---|
| C07C 51/14 | (2006.01) | |
| C07C 51/305 | (2006.01) | |
| C07C 67/42 | (2006.01) | |
| C07C 29/132 | (2006.01) | |
| C07C 209/26 | (2006.01) | |
| C07D 317/12 | (2006.01) | |
| C07D 319/06 | (2006.01) | |
| B01J 31/18 | (2006.01) | |
| C08G 69/28 | (2006.01) | |

(52) U.S. Cl.
CPC .............. *C07C 51/14* (2013.01); *B01J 31/185* (2013.01); *B01J 31/186* (2013.01); *C07C 29/132* (2013.01); *C07C 51/305* (2013.01); *C07C 67/42* (2013.01); *C07C 209/26* (2013.01); *C07D 317/12* (2013.01); *C07D 319/06* (2013.01); *C08G 69/28* (2013.01); *B01J 2231/321* (2013.01); *B01J 2231/349* (2013.01); *B01J 2531/822* (2013.01); *B01J 2540/10* (2013.01)

(58) Field of Classification Search
CPC ......... C07C 51/14; C07C 67/42; C07C 31/20; C07C 55/14; C07C 211/12; C07D 317/12
See application file for complete search history.

(56) References Cited

U.S. PATENT DOCUMENTS

| | | | |
|---|---|---|---|
| 3,947,503 A * | 3/1976 | Kummer ............... | C07C 29/141 568/866 |
| 4,778,929 A | 10/1988 | Zehner et al. | |
| 5,312,996 A | 5/1994 | Packett | |
| 5,728,893 A | 3/1998 | Becker et al. | |
| 6,642,420 B1 | 11/2003 | Zehner et al. | |
| 6,881,867 B2 | 4/2005 | Ahlers et al. | |
| 6,977,312 B2 | 12/2005 | Ahlers et al. | |
| 7,015,361 B2 | 3/2006 | Zehner et al. | |
| 7,145,042 B2 | 12/2006 | Volland et al. | |
| 7,173,138 B2 | 2/2007 | Ahlers et al. | |
| 8,110,709 B2 | 2/2012 | Papp et al. | |
| 2016/0264691 A1 | 9/2016 | Maitro-Vogel et al. | |
| 2016/0304415 A1 | 10/2016 | Schwartztrauber et al. | |
| 2017/0044084 A1 | 2/2017 | Schelwies et al. | |
| 2017/0066704 A1 | 3/2017 | Limburg et al. | |
| 2017/0175267 A1 | 6/2017 | Strautmann et al. | |
| 2017/0233865 A1 | 8/2017 | Strautmann et al. | |
| 2017/0355642 A1 | 12/2017 | Ernst et al. | |
| 2018/0057437 A1 | 3/2018 | Schelwies et al. | |

FOREIGN PATENT DOCUMENTS

| | | |
|---|---|---|
| AU | 2002324067 A1 | 3/2003 |
| DE | 10052462 A1 | 5/2002 |
| DE | 10342760 A1 | 3/2004 |
| EP | 423769 A2 | 4/1991 |

(Continued)

OTHER PUBLICATIONS

U.S. Appl. No. 15/573,276, BASF SE
U.S. Appl. No. 15/746,183, BASF SE
U.S. Appl. No. 15/136,112, BASF SE
U.S. Appl. No. 15/577,393, BASF SE
U.S. Appl. No. 15/571,274, BASF SE
U.S. Appl. No. 15/743,153, BASF SE (Continued)

*Primary Examiner* — Paul A Zucker
(74) *Attorney, Agent, or Firm* — Faegre Drinker Biddle & Reath LLP

(57) ABSTRACT

The invention relates to a process for the production of 1,6-difunctionalized hexane derivatives from 1,3-diunsaturated hydrocarbons, preferably butadiene, wherein a hydroformylation with carbon monoxide and hydrogen is performed in the presence of an at least dihydric alkanol and during the hydroformylation the temperature is increased. The reaction yields the acetals of the 1,6-hexanedial derivatives which are isolated and further reacted to obtain the desired 1,6-difunctionalized hexane derivatives, in particular 1,6-hexanediamine, 1,6-hexanediol and adipic acid.

28 Claims, No Drawings

(56) References Cited

FOREIGN PATENT DOCUMENTS

| EP | 0577042 A1 | 1/1994 |
|---|---|---|
| EP | 1114017 A1 | 7/2001 |
| EP | 1231198 A1 | 8/2002 |
| WO | WO-0009467 A1 | 2/2000 |
| WO | WO-0158589 A1 | 8/2001 |
| WO | WO-0222261 A2 | 3/2002 |
| WO | WO-02083695 A1 | 10/2002 |
| WO | WO-03018192 A2 | 3/2003 |
| WO | WO-2004026803 A1 | 4/2004 |
| WO | WO-2005009934 A2 | 2/2005 |
| WO | WO-2005039762 A1 | 5/2005 |
| WO | WO-2005063730 A1 | 7/2005 |

OTHER PUBLICATIONS

International Search Report for PCT/EP2016/074347 dated Jan. 25, 2017.
Written Opinion of the International Searching Authority for PCT/EP2016/074347 dated Jan. 25, 2017.

* cited by examiner

HYDROFORMYLATION PROCESS FOR PRODUCING 1,6-DISUBSTITUTED HEXANE DERIVATIVES

CROSS-REFERENCE TO RELATED APPLICATIONS

This application is a national stage application (under 35 U.S.C. § 371) of PCT/EP2016/074347, filed Oct. 11, 2016, which claims benefit of European Application No. 15189341.9, filed Oct. 12, 2015, both of which are incorporated herein by reference in their entirety.

FIELD OF THE INVENTION

The invention relates to a process for the production of 1,6-difunctionalized hexane derivatives from 1,3-diunsaturated hydrocarbons, preferably butadiene. The invention also relates to a process for the production of polyamide 6.6.

BACKGROUND OF THE INVENTION 1,6-Difunctionalized hexane derivatives, in particular 1,6-hexanediamine, 1,6-hexanediol and adipic acid, are valuable compounds which are produced on a large scale in the chemical industry. These compounds are of commercial interest in particular for the production of polymers like polyamides, for example polyamide 6.6, polyesters and polyurethanes.

1,6-Hexanediamine is produced on a large scale in hydrocyanation reactions of butadiene with hydrogen cyanide to obtain adipodinitrile followed by a hydrogenation reaction. This process of the prior art particularly suffers from the use of hydrogen cyanide which is an expensive and toxic compound.

Adipic acid is produced in the industry mainly via oxidation of cyclohexanol with nitric acid. This process of the prior art is disadvantageous because nitrogen oxides are formed during the process from the nitric acid which have to be destroyed or employed in other processes. Furthermore, cyclohexanol is an expensive compound. The hydroxycarboxylation of butadiene with carbon monoxide and water to obtain adipic acid is known in the prior art. However, this process was never employed on a larger scale in the industry because it suffers from low selectivities for adipic acid and problems concerning its isolation.

1,6-Hexanediol is largely produced via hydrogenation of adipic acid. However, adipic acid is mainly produced by the process mentioned above. Therefore, the production of 1,6-hexanediol is connected with the same disadvantages.

In order to overcome the disadvantages of the processes for the production of select 1,6-difunctionalized hexane derivatives, different approaches have been suggested in the prior art.

U.S. Pat. No. 3,947,503 discloses a multi-step process for the production of 1,6-hexanediol from butadiene. In the first step, butadiene is subjected to a reaction with carbon monoxide and hydrogen in the presence of a rhodium complex and an alkanol or alkanediol to obtain the mono-acetal of 3-pentenal. In the second step, the mono-acetal of 3-pentenal is reacted with carbon monoxide and hydrogen in the presence of a cobalt complex. In the third step, the resulting mixture is subjected to a hydrogenation reaction in the presence of a hydrogenation catalyst. This process is disadvantageous for several reasons. It requires many steps and the yield of 1,6-hexanediol based on the starting material butadiene is low. In this process, a high amount of undesirable by-products is formed. The regioselectivity for 1,6-hexanediol is not satisfactory. Further, at least two different catalysts are necessary for this process. This process is also limited to the production of 1,6-hexanediol.

U.S. Pat. No. 5,312,996 discloses a process for the production of 1,6-hexanedial by the reaction of butadiene with carbon monoxide and hydrogen under catalytic reaction of rhodium complexes. Also reactions in the presence of diols are described. The yield of 1,6-hexanedial based on the starting material butadiene is low. A high amount of undesirable by-products is formed, in particular unsaturated and saturated mono-acetals and branched diacetals. The regioselectivity for 1,6-hexanedial is not satisfactory. A process for the production of 1,6-hexanediamine is not described.

The processes of the prior art are connected with disadvantages. The 1,6-difunctionalized hexane derivatives are obtained in low regioselectivities and low yields in the processes of the prior art. In known hydroformylations of 1,3-diunsaturated compounds, in particular butadiene, the regioselectivity for the 1,6-isomer of the dialdehyde over the undesirable 1,2-, 1,3- and 1,4-isomers of the dialdehyde is generally not satisfactory. The processes of the prior art yield a number of by-products.

In the hydroformylation of butadiene, these are particularly mono-unsaturated pentenals, pentanal and the undesirable regioisomers 1,2-hexanedial, 1,3-hexanedial and 1,4-hexanedial. The processes of the prior art are limited to the production of only select 1,6-difunctionalized hexane derivatives, in particular 1,6-hexanediol. Further, many of the processes of the prior art are energy and time consuming multi-step reactions.

Accordingly, it is an object of the invention to provide a process for the production of 1,6-difunctionalized hexane derivatives from 1,3-diunsaturated hydrocarbons, in particular butadiene, with a high regioselectivity for the 1,6-difunctionalized hexane derivatives. The process should be versatile and provide an universal route to different 1,6-difunctionalized hexane derivatives. With the process it should be possible to provide the 1,6-difunctionalized hexane derivatives in high yield. The process should particularly allow for the production of 1,6-hexanediamine, 1,6-hexanediol and adipic acid from butadiene with a high regioselectivity. With the process it should particularly be possible to obtain 1,6-hexanediamine, 1,6-hexanediol and adipic acid in high yield. Very particularly, it should be possible to obtain 1,6-hexanediamine in the process in high yield. The process should be performed economically without the need for many reaction steps.

The object of the invention is solved by a process wherein a 1,3-diunsaturated hydrocarbon, preferably butadiene, is subjected to a hydroformylation with carbon monoxide and hydrogen in the presence of a transition metal catalyst and an at least dihydric alkanol which can form an acetal with an aldehyde group, wherein during the hydroformylation the temperature is increased for at least 10° C. to obtain the mono-acetal and/or the di-acetal of the 1,6-hexanedial derivative. The acetals of the 1,6-hexanedial derivative are separated and further reacted to obtain the desired 1,6-difunctionalized hexane derivatives.

Surprisingly, it was found that the acetals of the 1,6-hexanedial derivatives can be obtained with a high selectivity for the 1,6-regioisomers and a high yield when an at least dihydric alkanol, which can form an acetal with an aldehyde group, is present during the hydroformylation of the 1,3-diunsaturated hydrocarbon with carbon monoxide and hydrogen and during the hydroformylation the temperature is increased for at least 10° C. The regioselectivity and the yield can be even further improved when during the hydroformylation the pressure of the gas mixture of carbon monoxide and hydrogen in decreased. The acetals of the 1,6-hexanedial derivatives can be separated, for example by simple distillation, and beneficially be employed as a starting material in further reactions, preferably an amination with an ammonia source, a hydrogenation or an oxidation, to obtain the desired 1,6-difunctionalized hexane derivatives, in particular 1,6-hexanediamine, 1,6-hexanediol and adipic acid.

SUMMARY OF THE INVENTION

Accordingly, the invention relates to a process for the production of a compound of the formula (I)

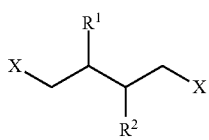
(I)

wherein
X are both $CH_2NH_2$, $CH_2OH$ or $COOH$,
$R^1$ and $R^2$ are independently from each other hydrogen or linear or branched $C_1$-$C_4$-alkyl,
comprising the following steps:
i) subjecting at least one compound of the formula (II)

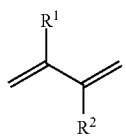
(II)

wherein $R^1$ and $R^2$ have the same meaning as in formula (I),
to a hydroformylation with carbon monoxide and hydrogen in the presence of at least one transition metal catalyst,
wherein the hydroformylation is performed in the presence of at least one alkanol of the formula (III)

HO—Z—OH (III)

wherein
Z is a hydrocarbon chain having 2 or 3 carbon atoms which is unsubstituted or substituted and which may be part of a carbocycle, a heterocycle or an aromatic or heteroaromatic ring,
wherein during the hydroformylation the temperature is increased for at least 10° C. from a temperature $T_1$ to a temperature $T_2$,
to obtain a reaction mixture comprising at least one compound selected from the compounds of the formula (IV.a) and (IV.b),

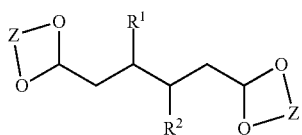
(IV.a)

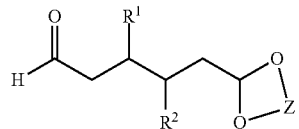
(IV.b)

wherein
Z has the same meaning as in formula (III), and
$R^1$ and $R^2$ have the same meaning as in formula (I),
ii) subjecting the reaction mixture obtained in step i) to a separation to obtain a fraction enriched with at least one compound selected from the compounds of the formula (IV.a) and (IV.b) and a fraction depleted with at least one compound selected from the compounds of the formula (IV.a) and (IV.b),
iii) optionally recycling at least partially the fraction depleted with at least one compound selected from the compounds of the formula (IV.a) and (IV.b) obtained in step ii) to step i), and
iv) subjecting the fraction enriched with at least one compound selected from the compounds of the formula (IV.a) and (IV.b) obtained in step ii) to a reaction in which the acetal groups in the compounds of the formula (IV.a) and (IV.b) are reacted to obtain the compound of the formula (I).

The invention also relates to a process for the production of polyamide 6.6, wherein butadiene is employed as the at least one compound of the formula (II) in the above process, wherein the reaction in step iv) is an amination with an ammonia source to obtain 1,6-hexanediamine which is reacted with adipic acid to obtain the polyamide 6.6.

DETAILED DESCRIPTION OF THE INVENTION

In step i) of the process of the invention, at least one compound of the formula (II) is subjected to a hydroformylation with carbon monoxide and hydrogen in the presence of at least one alkanol of the formula (III) and at least one transition metal catalyst.

The at least one compound of the formula (II) which is employed in step i) of the process of the invention is a 1,3-diunsaturated hydrocarbon which is unsubstituted or substituted with linear or branched $C_1$-$C_4$-alkyl in the 2- and 3-position. Preferably, the at least one compound of the formula (II) is selected from butadiene, isoprene and 2,3-dimethylbutadiene. Most preferred is butadiene.

The at least one alkanol of the formula (III) which is present in step i) of the process of the invention is an at least dihydric alkanol which is able to form stable acetals with the aldehyde groups formed in the compounds of the formula (II) under the conditions of the hydroformylation reaction. The at least one alkanol of the formula (III) is an at least dihydric alkanol in which two hydroxyl groups are linked over a hydrocarbon chain having 2 or 3 carbon atoms which is unsubstituted or substituted and which may be part of a carbocycle, a heterocycle or an aromatic or heteroaromatic ring. Suitable alkanols of the formula (III) are selected from 1,2-ethanediol, 1,2-propanediol, 1,3-propanediol, 2-methyl-1,3-propanediol, 2,2-dimethyl-1,3-propanediol, 1,2,3-propanediol (glycerol), diglycerol (a mixture of glycerol dimers coupled at primary and secondary hydroxyl groups), 2,2-dimethyl-1,3-propanediol, 3-mercaptopropane-1,2-diol (thioglycerol), dithiothreitol, 1,1,1-trimethylolpropane, 1,2- butanediol, 1,3-butanediol, 2,4-butanediol, 2,4-dimethyl-2,4-butanediol, pentaerythritol, cyclohexane-1,2-diol, 1,4-dioxane-2,3-diol, 1,2,3-butanetriol, 1,3,4-butanetriol, 1,2,3-heptanetriol, 4-menthane-1,7,8-triol, 3-butene-1,2-diol, benzene-1,2-diol (catechol), 3-chlorocatechol, indane-1,2-diol, tartaric acid and pentose and hexose sugars including mannitol, sorbitol, xylitol, threitol, erythritol, maltitol and lactitol. Particularly preferred alkanols of the formula (III) are 1,2-ethanediol, 1,2-propanediol, 1,3-propanediol, 2-methyl-1,3-propanediol, 2,2-dimethyl-1,3-propanediol, 2,4-butanediol, 2,4-dimethyl-2,4-butanediol and benzene-1,2-diol (catechol). Most preferred is 1,2-ethanediol.

Preferably, the at least one alkanol of the formula (III) is employed in excess compared to the at least one compound of the formula (II), preferably butadiene. The molar ratio of the at least one compound of the formula (II) to the at least one alkanol of the formula (III) is preferably in the range from 1:1 to 1:100.

In the process of the present invention, at least one transition metal catalyst is employed. In principle, all transition metal catalysts which are known to catalyze hydroformylation reactions can be employed in the process of the invention. Such catalysts are described, for example, in WO 01/58589, WO 02/083695, WO 02/22261, WO 03/018192, WO 2004/026803, WO 2005/009934, WO 2005/039762, WO 2005/063730, DE 103 42 760 A1 and DE 100 52 462 A1, in particular in DE 100 52 462 A1 and WO 02/083695.

The at least one transition metal catalyst comprises at least one transition metal and at least one ligand, preferably a phosphorous-containing bidentate ligand.

The at least one transition metal catalyst preferably comprises at least one transition metal selected from the transition metals of the groups 8, 9 and 10 of the periodic table of the elements according to IUPAC. Preferably, the at least one transition metal is selected from Co, Ru, Ir, Rh, Ni, Pd, Pt and mixtures thereof. More preferably, the at least one transition metal is Rh.

The at least one transition metal catalyst preferably comprises at least one ligand which comprises at least one atom selected from P, As and Sb. More preferably, the at least one ligand comprises at least one P atom.

Preferably, the at least one transition metal K comprises at least one bidentate ligand which is bound over two P atoms to the transition metal and which has a natural bite-angle in the range from 90° to 130°, preferably 100° to 120°. The expression "natural bite-angle" is known to a person skilled in the art and explained for example in P. W. N. M. van Leeuwen et al., Chem. Rev. 2000, 2741.

In the sense of the invention, the expression "alkyl" means straight and branched alkyl groups. Preferred are straight or branched $C_1$-$C_{20}$-alkyl groups, more preferably $C_1$-$C_{12}$-alkyl groups, even more preferably $C_1$-$C_8$-alkyl groups and in particular $C_1$-$C_6$-alkyl groups. Examples of alkyl groups are particularly methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl and decyl.

The expression "alkyl" comprises also substituted alkyl groups, which may carry 1, 2, 3, 4 or 5 substituents, preferably 1, 2 or 3 substituents and particularly preferably 1 substituent, selected from the groups cycloalkyl, aryl, hetaryl, halogen, $NE^1E^2$, $NE^1E^2E^{3+}$, COOH, carboxylate, $SO_3H$ and sulfonate. A preferred fluorinated alkyl group is trifluoromethyl. The expression "alkyl" also comprises alkyl groups which are interrupted by one or more non-adjacent oxygen atoms, preferably alkoxyalkyl.

The expression "alkylene" in the sense of the present invention stands for straight or branched alkanediyl groups with preferably 1 to 6 carbon atoms. These are methylene (—$CH_2$—), ethylene (—$CH_2$—$CH_2$—), n-propylene (—$CH_2$—$CH_2$—$CH_2$—), isopropylene (—$CH_2$—CH($CH_3$)—), etc.

The expression "cycloalkyl" in the sense of the present invention comprises unsubstituted and substituted cycloalkyl groups, preferably $C_5$-$C_7$-cycloalkyl groups like cyclopentyl, cyclohexyl or cycloheptyl, which in case they are substituted may carry 1, 2, 3, 4 or 5 substituents, preferably 1, 2 or 3 substituents and particularly preferred 1 substituent selected from the groups alkyl, alkoxy and halogen.

The expression "heterocycloalkyl" in the sense of the present invention comprises saturated or partially unsaturated cycloaliphatic groups with preferably 4 to 7, more preferably 5 or 6 ring atoms, in which 1, 2, 3 or 4 ring atoms may be substituted with heteroatoms, preferably selected from the elements oxygen, nitrogen and sulfur and which are optionally substituted. In case they are substituted, these heterocycloaliphatic groups carry preferably 1, 2 or 3 substituents, more preferably 1 or 2 substituents and in particular 1 substituent. These substituents are preferably selected from alkyl, cycloalkyl, aryl, COOR (R=H, alkyl, cycloalkyl, aryl), $COO^-M^+$ and $NE^1E^2$, more preferably alkyl. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl and dioxanyl.

The expression "aryl" in the sense of the present invention comprises unsubstituted and substituted aryl groups and preferably stands for phenyl, tolyl, xylyl, mesityl, naphthyl, fluorenyl, anthracenyl, phenanthrenyl or naphthacenyl, more preferably phenyl or naphthyl. In case these aryl groups are substituted they may carry preferably 1, 2, 3, 4 or 5 substituents, more preferably 1, 2 or 3 substituents and particularly preferred 1 substituent. These substituents are preferably selected from the groups alkyl, alkoxy, carboxyl, carboxylate, trifluoromethyl, —$SO_3H$, sulfonate, $NE^1E^2$, alkylene-$NE^1E^2$, nitro, cyano and halogen. A preferred fluorinated aryl group is pentafluorophenyl.

The expression "hetaryl" in the sense of the present invention comprises unsubstituted or substituted heterocycloaromatic groups, preferably pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl in which in case these heterocycloaromatic groups are substituted they may carry preferably 1, 2 or 3 substituents selected from the groups alkyl, alkoxy, carboxyl, carboxylate, —$SO_3H$, sulfonate, $NE^1E^2$, alkylene-$NE^1E^2$, trifluoromethyl and halogen. A preferred substituted indolyl group is 3-methylindolyl.

Carboxylate and sulfonate in the sense of the present invention preferably stand for a derivative of a carboxylic acid function or a sulfonic acid function, in particular a metal carboxylate or metal sulfonate, a carboxylic acid ester or sulfonic acid ester or a carboxylic acid amide or sulfonic acid amide. Particularly preferred are esters with $C_1$-$C_4$-alkanols like methanol, ethanol, n-propanol, isopropanol, n-butanol, sec-butanol and tert-butanol. Preferred are also the primary amides and their N-alkyl and N,N-dialkyl derivatives.

The above statements regarding the expressions "alkyl", "cycloalkyl", "aryl", "heterocycloalkyl" and "hetaryl" apply accordingly to the expressions "alkoxy", "cycloalkoxy", "aryloxy", "heterocycloalkoxy" and "hetaryloxy".

The expression "acyl" in the sense of the present invention stands for alkanoyl groups or aroyl groups with preferably 2 to 11, more preferably 2 to 8 carbon atoms, for example acetyl, propanoyl, butanoyl, pentanoyl, hexanoyl, heptanoyl, 2-ethylhexanoyl, 2-propylheptanoyl, benzoyl and naphthoyl.

The groups $NE^1E^2$, $NE^4E^5$, $NE^7E^8$, $NE^{10}E^{11}$, $NE^{13}E^{14}$, $NE^{16}E^{17}$, $NE^{19}E^{20}$ and $NE^{22}E^{23}$ are preferably selected from N,N-dimethylamino, N,N-diethylamino, N,N-dipropylamino, N,N-diisopropylamino, N,N-di-n-butylamino, N,N-di-tert-butylamino, N,N-dicyclohexylamino and N,N-diphenylamino.

Halogen stands for fluorine, chlorine, bromine or iodine, preferably fluorine, chlorine or bromine.

$M^+$ stands for a cation equivalent, which means a monovalent cation or the part of a polyvalent cation representing a positive single charge. The cation $M^+$ is only a counter ion which neutralizes negatively charged substituents like the $COO^-$ or the sulfonate group and which can principally be selected arbitrarily. Preferred are alkaline metal ions, in particular $Na^+$, $K^+$ and $Li^+$ ions, or onium ions like ammonium ions, mono-, di-, tri-, tetraalkylammonium ions, phosphonium ions, tetraalkylphosphonium ions and tetraarylphosphonium ions.

The same applies to the anion equivalent $X^-$ which is only a counter ion for positively charged substituents like the ammonium group and which can principally be selected arbitrarily among monovalent anions and the parts of polyvalent anions which correspond to a single negative charge. Preferred are halogenides $X^-$, in particular chloride and bromide. Also preferred are sulfates and sulfonates, in particular $SO_4^{2-}$, tosylate, trifluoromethane sulfonate and methylsulfonate.

y stands for an integer in the range from 1 to 240, preferably in the range from 1 to 120. More preferably, y stands for an integer in the range from 3 to 120.

Condensed ring systems are aromatic, heteroaromatic or cyclic compounds which have fused-on rings obtained via anellation. Condensed ring systems consist of two, three or more than three rings. Depending on the type of connection, one distinguishes between ortho-anellation and peri-anellation. In case of ortho-anellation each ring has two atoms in common with each adjacent ring. In case of peri-anellation a carbon atoms belongs to more than two rings. Preferred among the condensed ring systems are ortho-condensed ring systems.

In a preferred embodiment of the invention, the at least one transition metal catalyst comprises at least one ligand of the formula (V)

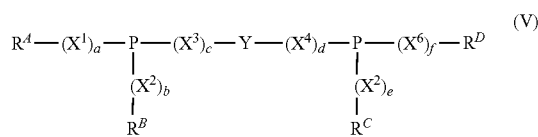

wherein $R^A$, $R^B$, $R^C$ and $R^D$ are independently from each other alkyl, cycloalkyl, heterocycloalkyl, aryl or hetaryl, wherein the alkyl radicals may carry 1, 2, 3, 4 or 5 substituents selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, carboxyl, $SO_3H$, sulfonate, $NE^1E^2$, $NE^1E^2E^{3+}X^-$, halogen, nitro, formyl, acyl and cyano, wherein $E^1$, $E^2$ and $E^3$ are the same or different and are selected from hydrogen, alkyl, cycloalkyl, and aryl and $X^-$ is an anion equivalent, and wherein the radicals cycloalkyl, heterocycloalkyl, aryl and hetaryl $R^A$, $R^B$, $R^C$ and $R^D$ may carry 1, 2, 3, 4 or 5 substituents selected from alkyl and the substituents mentioned for the alkyl radicals $R^A$, $R^B$, $R^C$ and $R^D$ before, or $R^A$ and $R^B$ and/or $R^C$ and $R^D$ together with the P atom and, if present, the groups $X^1$, $X^2$, $X^5$ and $X^6$ to which they are bound, are a 5- to 8-membered heterocycle, which is optionally fused with one, two or three groups selected from cycloalkyl, heterocycloalkyl, aryl and heteroaryl, wherein the heterocycle and, if present, the fused-on groups independently from each other may each carry 1, 2, 3 or 4 substituents selected from alkyl, cycloalkyl, heterocycloalkyl, aryl, hetaryl, hydroxy, mercapto, polyalkylene oxide, polyalkyleneimine, alkoxy, halogen, carboxyl, $SO_3H$, sulfonate, $NE^4E^5$, $NE^4E^5E^{6+}X^-$, nitro, alkoxycarbonyl, formyl, acyl and cyano, wherein $E^4$, $E^5$ and $E^6$ are the same or different and are selected from hydrogen, alkyl, cycloalkyl and aryl and $X^-$ is an anion equivalent, $X^1$, $X^2$, $X^3$, $X^4$, $X^5$ and $X^6$ are independently from each other O, S, $SiR^xR^y$ or $NR^z$, wherein $R^x$, $R^y$ and $R^z$ are independently from each other hydrogen, alkyl, cycloalkyl, heterocycloalkyl, aryl or hetaryl, Y is a divalent bridging group which contains carbon atoms, and a, b, c, d, e and f are independently from each other 0 or 1.

In another preferred embodiment of the invention, the at least one transition metal catalyst comprises at least one ligand of the formula (V.1)

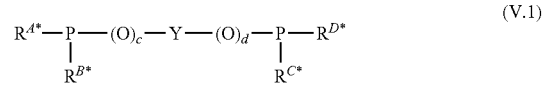

wherein

Y is a divalent bridging group which contains carbon atoms, c and d are independently from each other 0 or 1, and the radicals $R^{A*}$, $R^{B*}$, $R^{C*}$ and $R^{D*}$ are independently from each other selected from the groups of the formula (VI.a) to (VI.k)

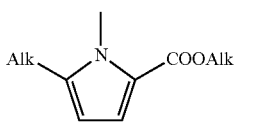
(VI.b)

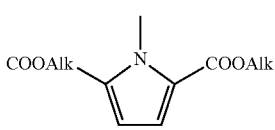
(VI.c)

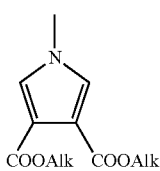
(VI.d)

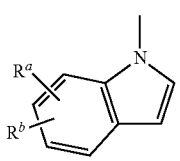
(VI.e)

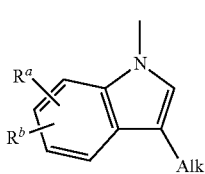
(VI.f)

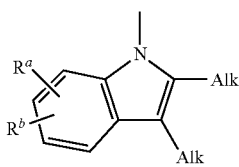
(VI.g)

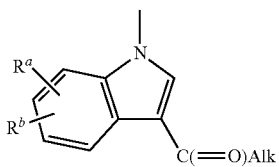
(VI.h)

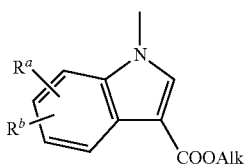
(VI.i)

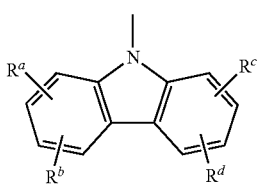
(VI.k)

wherein

Alk is a $C_1$-$C_4$-alkyl group, and $R^a$, $R^b$, $R^c$ and $R^d$ are independently from each other hydrogen, $C_1$-$C_4$-alkyl, $C_1$-$C_4$-alkoxy, formyl, acyl, halogen, $C_1$-$C_4$-alkoxycarbonyl or carboxyl. Particularly preferred groups $R^a$, $R^b$, $R^c$ and $R^d$ are methyl, ethyl, n-propyl, isopropyl, n-butyl, tert-butyl and trifluoromethyl.

In another preferred embodiment of the invention, the at least one transition metal catalyst comprises at least one ligand of the formula (VII)

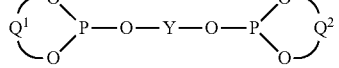
(VII)

wherein

Y is a divalent bridging group which contains carbon atoms, $Q^1$ and $Q^2$ are independently from each other a divalent bridging group of the formula (VIII),

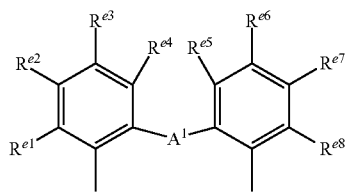
(VIII)

wherein $R^{e1}$, $R^{e2}$, $R^{e3}$, $R^{e4}$, $R^{e5}$, $R^{e6}$, $R^{e7}$ and $R^{e8}$ are independently from each other hydrogen, in each case unsubstituted or substituted alkyl, alkoxy, cycloalkyl, cycloalkoxy, heterocycloalkyl, heterocycloalkoxy, aryl, aryloxy, hetaryl, hetaryloxy, halogen, hydroxy, mercapto, cyano, nitro, formyl, acyl, carboxy, carboxylate, alkylcarbonyloxy, carbamoyl, $SO_3H$, sulfonate or $NE^{12}E^{13}$, wherein $E^{12}$ and $E^{13}$ are the same or different and are selected from hydrogen, alkyl, cycloalkyl, heterocycloalkyl, aryl and hetaryl, wherein two adjacent radicals $R^{e1}$ to $R^{e8}$ together with the carbon atoms of the benzene ring to which they are bound may also be a condensed ring system with 1, 2 or 3 further rings, and $A^1$ is a single bond, O, S, $NR^{a31}$, $SiR^{a32}R^{a33}$ or $C_1$-$C_4$-alkylene, which may have a double bond and/or which may be substituted with alkyl, cycloalkyl, heterocycloalkyl, aryl or hetaryl or which may be interrupted by O, S, $NR^{a31}$ or $SiR^{a32}R^{a33}$, wherein $R^{a31}$, $R^{a32}$ and $R^{a33}$ are independently from each other hydrogen, alkyl, cycloalkyl, heterocycloalkyl, aryl or hetaryl.

The divalent bridging group Y is a divalent bridging group which contains carbon atoms. The divalent bridging group Y is preferably selected from the groups of the formula (IX.a) to (IX.u)

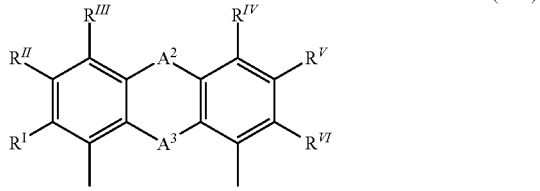
(IX.a)

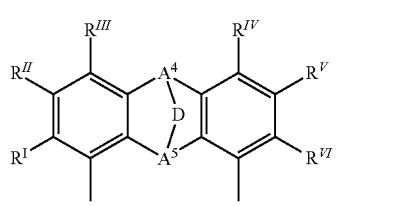
(IX.b)
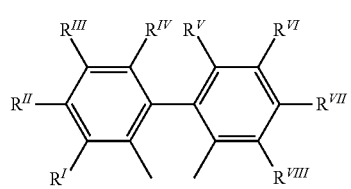
(IX.c)
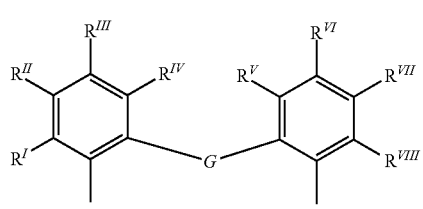
(IX.d)
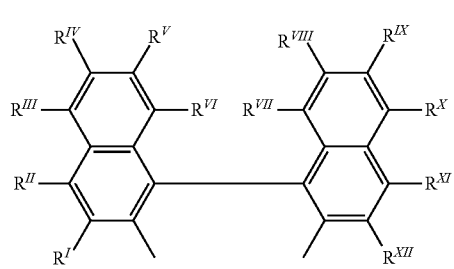
(IX.e)
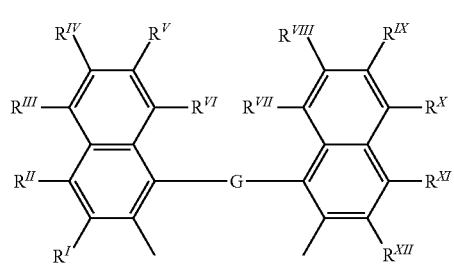
(IX.f)
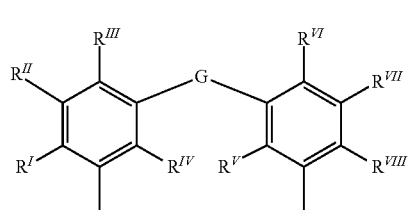
(IX.g)
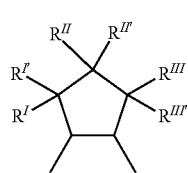
(IX.h)
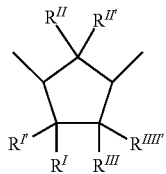
(IX.i)
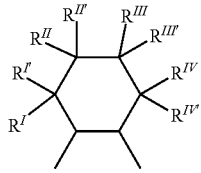
(IX.k)
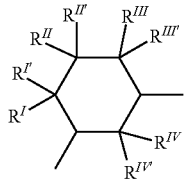
(IX.l)
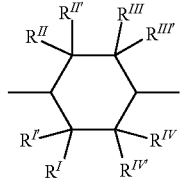
(IX.m)
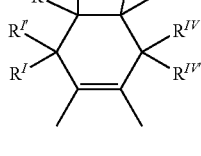
(IX.n)
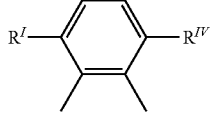
(IX.o)
(IX.p)
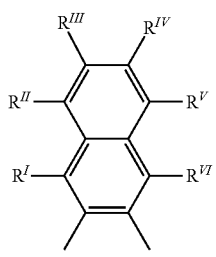
(IX.q)

-continued

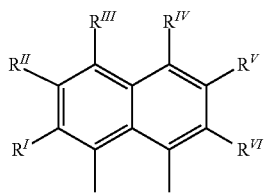

(IX.r)

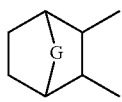

(IX.s)

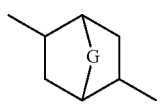

(IX.t)

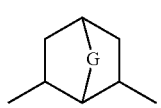

(IX.u)

wherein
$R^I$, $R^{I'}$, $R^{II}$, $R^{II'}$, $R^{III}$, $R^{III'}$, $R^{IV}$, $R^{IV'}$, $R^V$, $R^{VI}$, $R^{VII}$, $R^{VIII}$, $R^{IX}$, $R^X$, $R^{XI}$, and $R^{XII}$ are each, independently from each other, hydrogen, alkyl, cycloalkyl, heterocycloalkyl, aryl, hetaryl, hydroxy, thiol, polyalkylene oxide, polyalkylenimine, alkoxy, halogen, $SO_3H$, sulfonate, $NE^1E^2$, alkylene-$NE^1E^2$, nitro, alkoxycarbonyl, carboxyl, acyl or cyano, wherein $E^1$ and $E^2$ are identical or different and are selected from hydrogen, alkyl, cycloalkyl and aryl, G is O, S, $NR^\delta$ or $SiR^\delta R^\epsilon$, wherein
  $R^\delta$ and $R^\epsilon$ are each, independently from each other, hydrogen, alkyl, cycloalkyl, heterocycloalkyl, aryl or hetaryl,
or G is a $C_1$-$C_4$-alkylene bridge which may have a double bond and/or which carries an alkyl, cycloalkyl, heterocycloalkyl, aryl or hetaryl substituent,
or G is a $C_2$-$C_4$-alkylene bridge which is interrupted by O, S or $NR^\delta$ or $SiR^\delta R^\epsilon$, wherein in the groups of the formula (IX.a) and (IX.b), two adjacent radicals $R^I$ to $R^{VI}$ together with the carbon atoms of the benzene ring to which they are bound may also form a fused ring system having 1, 2 or 3 further rings, wherein in the groups of the formula (IX.h) to (IX.n), two geminal radicals $R^I$, $R^{I'}$; $R^{II}$, $R^{II'}$; $R^{III}$, $R^{III'}$ and/or $R^{IV}$, $R^{IV'}$ may also represent oxo or a ketal thereof, $A^2$ and $A^3$ are each, independently from each other, O, S, $SiR^\Phi R^\gamma$, $NR^\eta$ or $CR^\iota R^\kappa$, wherein $R^\Phi$, $R^\gamma$, $R^\eta$, $R^\iota$ and $R^\kappa$ are each, independently from each other, hydrogen, alkyl, cycloalkyl, heterocycloalkyl, aryl or hetaryl, $A^4$ and $A^5$ are each, independently from each other, $SiR^\Phi$, N or $CR^\iota$, D is a divalent bridging group of the formula

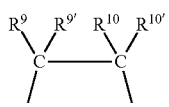

wherein
$R^9$, $R^{9'}$, $R^{10}$ and $R^{10'}$ are each, independently from each other, hydrogen, alkyl, cycloalkyl, aryl, halogen, trifluoromethyl, carboxyl, carboxylate or cyano, wherein $R^{9'}$ together with $R^{10'}$ may also represent the second bond of a double bond between the two carbon atoms to which $R^{9'}$ and $R^{10'}$ are bound, and/or $R^9$ and $R^{10}$ together with the carbon atoms to which they are bound may also form a 4- to 8-membered carbocycle or heterocycle which may additionally be fused with one, two or three cycloalkyl, heterocycloalkyl, aryl or hetaryl groups, wherein the heterocycle and, if present, the fused-on groups may each carry, independently from each other, 1, 2, 3 or 4 substituents selected from alkyl, cycloalkyl, heterocycloalkyl, aryl, hetaryl, $COOR^f$, $COO^-M^+$, $SO_3R^f$, $SO_3$-$M^+$, $NE^4E^5$, alkylene-$NE^4E^5$, $NE^4E^5E^{6+}X^-$, alkylene-$NE^4E^5E^{6+}X^-$, $OR^f$, $SR^f$, $(CHR^eCH_2O)_yR^f$, $(CH_2N(E^4))_yR^f$, $(CH_2CH_2N(E^4))_yR^f$, halogen, trifluoromethyl, nitro, acyl and cyano, wherein
$R^f$, $E^4$, $E^5$ and $E^6$ are the same or different and are selected from hydrogen, alkyl, cycloalkyl and aryl, $R^e$ is hydrogen, methyl or ethyl, $M^+$ is a cation equivalent, $X^-$ is an anion equivalent, and y is an integer from 1 to 240.

Particularly preferred are divalent bridging groups Y of the formula (IX.b) and (IX.c).

In the preferred divalent bridging groups Y of the formula (IX.b), a particularly preferred divalent bridging group D is the ethylene group —$CH_2$—$CH_2$—. Accordingly, the divalent bridging groups Y of the formula (IX.b) have preferably a triptycene-like carbon skeleton.

In the preferred divalent bridging groups Y of the formula (IX.c), the substituents $R^I$ to $R^{VIII}$ are preferably selected from hydrogen, alkyl and alkoxy.

In a particularly preferred embodiment of the invention, the at least one transition metal catalyst comprises at least one ligand selected from the compounds of the formula (V.a) (tMe-Rucaphosphite) and (V.b) (Biphephos)

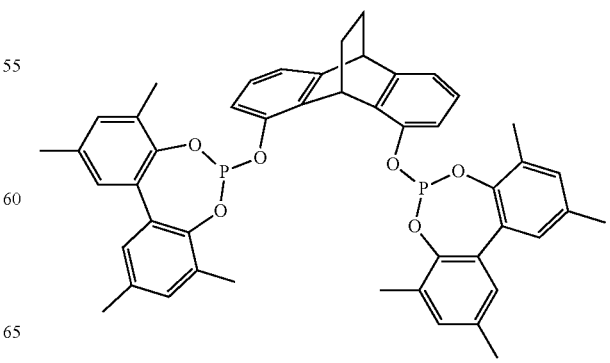

(V.a)

-continued

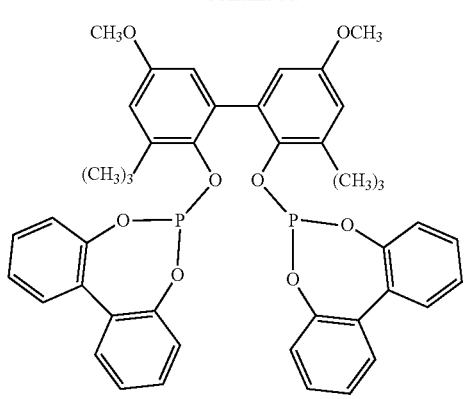

(V.b)

In addition to the ligands described before, the at least one transition metal catalyst can have at least one further ligand which is preferably selected from halogenides, amines, carboxylates, acetylacetonate, arylsulfonates or alkylsulfonates, hydride, CO, olefins, dienes, cycloolefines, nitriles, N-containing heterocycles, aromates and heteroaromates, ethers, $PF_3$, phosphols, phosphabenzenes and monodentate ligands selected from phosphines, phosphinites, phosphonites, phosphoramidites and phosphites. Additional ligands which are particularly preferred are hydride, carbonyl and triphenylphosphine. The at least one transition metal catalyst can contain more than one additional ligand which can also be different ligands. Particularly preferably the at least one transition metal catalyst contains hydride and carbonyl. In particular, the at least one transition metal catalyst contains one ligand of the formula (V), (V.1) or (VII) and hydride or one ligand of the formula (V), (V.1) or (VII) and carbonyl.

The amount of the transition metal in the at least one transition metal catalyst, preferably Rh, is preferably in the range from 0.1 to 5000 ppm based on the weight of the at least one transition metal catalyst.

The molar ratio of the preferred phosphorous-containing ligands, preferably a ligand of the formula (V), (V.1) or (VII), to the at least one transition metal is preferably in the range from 1:1 to 1000:1, more preferably in the range from 1:1 to 500:1.

The homogeneous transition metal catalysts can be produced beforehand and employed in their active form in the process of invention. The transition metal catalysts can also be produced from transition metal sources under addition of the ligands, preferably the ligands of the formula (V), (V.1) or (VII), under the reaction conditions of the hydroformylation. In a preferred embodiment, the at least one transition metal catalyst is produced in the reaction mixture of the hydroformylation wherein at least one of the ligands of the formula (V), (V.1) or (VII), a compound or a complex of the transition metal and optionally an activating agent are reacted in an inert solvent under the hydroformylation conditions.

Suitable transition metal sources are principally transition metals, transition metal compounds and transition metal complexes from which the transition metal catalyst is formed under the hydroformylation conditions.

Suitable as a transition metal sources are particularly rhodium compounds or rhodium complexes. Preferred rhodium compounds or rhodium complexes are rhodium(II) salts and rhodium(III) salts like rhodium(II) carboxylate and rhodium(III) carboxylate, rhodium(II) acetate and rhodium(III) acetate, etc. Further suitable are rhodium complexes like rhodiumbiscarbonylacetylacetonate, acetylacetonatobisethylenerhodium(I) acetylacetonatocyclooctadienylrhodium(I), acetylacetonatonorbornadienylrhodium(I), acetylacetonatocarbonyltriphenylphosphinerhodium(I), etc. Particularly preferred transition metal sources are selected from rhodiumbiscarbonylacetylacetonate, rhodium(II) acetate and rhodium(III) acetate.

According to the invention, during the hydroformylation in step i) the temperature is increased for at least 10° C. from a temperature $T_1$ to a temperature $T_2$. Preferably, the temperature is increased for at least 20° C., particularly preferably for at least 30° C.

$T_1$ is preferably at least 40° C. $T_2$ is preferably at least 110° C.

$T_1$ is preferably in the range from 40 to 100° C., more preferably in the range from 50 to 90° C. $T_2$ is preferably in the range from 110 to 150° C., more preferably in the range from 115 to 130° C.

In a preferred embodiment, $T_1$ is at least 40° C. and $T_2$ is at least 110° C. In this embodiment, it is preferred that $T_1$ is in the range from 40 to 100° C. and $T_2$ is in the range from 110 to 150° C. More preferably, $T_1$ is in the range from 50 to 90° C. and $T_2$ is in the range from 115 to 130° C.

Preferably, the temperature is increased from $T_1$ to $T_2$ with a heating rate of from 0.5 K per minute to 400 K per minute, more preferably of from 1 K per minute to 100 K per minute.

Preferably, the temperature is increased from $T_1$ to $T_2$ after at least 30 mol-%, preferably at least 40 mol-% and particularly preferably at least 50 mol-% of the double bond equivalents of the at least one compound of the formula (II) are reacted.

Preferably, the hydroformylation is performed at the temperature $T_1$ for a period which is shorter than the period in which the hydroformylation is performed at the temperature $T_2$. Preferably, the hydroformylation is performed at the temperature $T_1$ for a period of from 0.1 to 4 h, more preferably for a period of from 0.3 to 3 h. Preferably, the hydroformylation is performed at the temperature $T_2$ for a period of from 0.3 to 40 h, more preferably for a period of from 0.5 to 20 h.

In the hydroformylation of step i), a gas mixture of carbon monoxide and hydrogen is employed. The molar ratio of carbon monoxide to hydrogen can principally be varied over a broad range. The molar ratio of carbon monoxide to hydrogen is generally in the range from 5:95 to 70:30, preferably in the range from 40:60 to 60:40. Particularly preferably, a gas mixture of carbon monoxide and hydrogen is employed in step i) wherein the molar ratio of carbon monoxide to hydrogen is about 1:1.

The hydroformylation in step i) is generally performed at the partial pressure of the gas mixture of carbon monoxide and hydrogen at the respective reaction temperature. Preferably, the pressure of the gas mixture of carbon monoxide and hydrogen is in the range from 1 to 700 bar, more preferably from 1 to 600 bar and even more preferably from 1 to 300 bar.

In a preferred embodiment of the process of the invention, the pressure is decreased in step i). Preferably, the pressure is decreased for at least 5 bar, more preferably for at least 10 bar.

It is preferred that the pressure is decreased when the temperature $T_1$ is increased to the temperature $T_2$.

Preferably, the pressure is decreased after at least 30 mol-%, preferably at least 40 mol-% and particularly preferably at least 50 mol-% of the double bond equivalents of the at least one compound of the formula (II) are reacted.

In a preferred embodiment, the hydroformylation in step i) is performed at a pressure of the gas mixture of carbon monoxide and hydrogen which is in the range from 20 to 70 bar, preferably in the range from 25 to 50 bar, and the pressure is decreased during the hydroformylation to a pressure of the gas mixture of carbon monoxide and hydrogen in the range from 2 to 18 bar, preferably in the range from 5 to 15 bar. In this embodiment, the molar ratio of carbon monoxide to hydrogen is preferably about 1:1.

In a particularly preferred embodiment, the hydroformylation in step i) is performed at a temperature $T_1$ which is preferably in the range from 40 to 100° C., more preferably in the range from 50 to 90° C., and a pressure of the gas mixture of carbon monoxide and hydrogen in the range from 20 to 70 bar, preferably in the range from 25 to 50 bar, and the temperature is increased to a temperature $T_2$ which is preferably in the range from 110 to 150° C., more preferably in the range from 115 to 130° C., and a pressure of the gas mixture of carbon monoxide and hydrogen in the range from 2 to 18 bar, preferably in the range from 5 to 15 bar. In this embodiment, the molar ratio of carbon monoxide to hydrogen is preferably about 1:1.

The hydroformylation of step i) is generally performed in a reaction zone which may comprise one or more reactors which may be the same or different. In the simplest case, the reaction zone is formed by a single reactor. The reactors may have the same or different mixing characteristics. The reactors may be divided into two or more different sections by built-in components. In case the reaction zone is formed by two or more reactors, the reactors may be connected in any possible order, for example in parallel or in series. Suitable reactors are principally all reactors which can be employed for hydroformylation reactions, for example stirred reactors, bubble column reactors, for example those described in U.S. Pat. No. 4,778,929, circulation reactors, for example those described in EP-A 1 114 017, tube reactors, wherein the respective reactors may have different mixing characteristics as described in EP-A 423 769.

Further suitable reactors are compartmented reactors as described in EP-A 1 231 198 or U.S. Pat. No. 5,728,893. Suitable reactors are principally known to a person skilled in the art and are described for example in "Ullmanns Enzyklopädie der technischen Chemie", Vol. 1, 3rd edition, 1951, page 743 ff. Suitable pressure-resistant reactors are also known to a person skilled in the art and are described for example in "Ullmanns Enzyklopädie der technischen Chemie", Vol. 1, 3rd edition, 1951, page 769 ff. Preferably, for the process of the invention an autoclave is employed which may have an internal stirrer and an internal lining.

A person skilled in the art knows, in principle, how to perform a reaction with a gas mixture in which the temperature is increased during the reaction and will select the reactors and the combination of the reactors accordingly.

The hydroformylation of step i) can principally be performed continuously, semicontinuously or discontinuously.

In a preferred embodiment, the hydroformylation reaction in step i) is performed continuously. In this embodiment, the hydroformylation is preferably first performed in a reaction zone which has the temperature $T_1$ and then in a reaction zone which has the temperature $T_2$. For example, the hydroformylation can be performed in two reactors which have the different temperatures $T_1$ and $T_2$. The hydroformylation is first performed in the reactor with the temperature $T_1$ and then the reaction mixture is transferred to the reactor with the temperature $T_2$.

In another preferred embodiment, the hydroformylation reaction in step i) is performed discontinuously. In this embodiment, the hydroformylation can be performed in a single reactor. The temperature is then increased from $T_1$ to $T_2$ preferably by heating of the reactor, for example with an electrical heating.

The hydroformylation in step i) can be performed in a solvent which is inert under the reaction conditions. Suitable solvents are preferably aromates like toluene and xylenes, hydrocarbons and mixtures of hydrocarbons, esters of aliphatic carboxylic acids with alkanols, for example Texanol®, esters of aromatic carboxylic acids, for example $C_8$-$C_{13}$-dialkylphthalates and ethers, for example tert-butylmethyl ether or tetrahydrofurane. In case the preferred compounds of the formula (V), (V.1) or (VII) are sufficiently hydrophilic, also monohydric alkanols like methanol, ethanol, n-propanol, isopropanol, n-butanol and isobutanol or ketones like acetone or methylethylketone are preferred as solvents. In principle, also ionic liquids can be employed as solvents. Preferred ionic liquids are N,N'-dialkylimidazolium salts, for example N-butyl-N'-methylimidazolium salts, tetraalkylammonium salts, for example tetra-n-butylammonium salts, N-alkylpyridinium salts, for example N-butylpyridinium salts, tetraalkylphosphonium salts, for example trishexyl(tetradecyl)phosphonium salts, in particular the tetrafluoroborates, acetates, tetrachloroaluminates, hexafluorophosphates, chlorides and tosylates of these salts. In principle, also water or water-containing solvents can be employed as solvents in the hydroformylation.

Preferred water-containing solvents are mixtures of water with alkanols, preferably methanol, ethanol, n-propanol, isopropanol, n-butanol or isobutanol, or ketones, preferably acetone or methylethylketone.

In a preferred embodiment, no inert solvent is employed and step i) is performed in the at least one alkanol of the formula (III).

It is preferred to perform step i) of the invention in the presence of at least one acid. In principle, all acids can be employed which catalyze the formation of acetals from aldehydes and alkanols. Principally suitable acids are Bronsted acids, Lewis acids and mixtures thereof. Particularly preferred are Bronsted acids. Preferred examples of suitable acids are trifluoroacetic acid, formic acid, hydrochloric acid, sulfuric acid, nitric acid, acidic pyridinium salts and p-toluenesulfonic acid. Also preferred are acidic ion exchangers, in particular sulfonated polystyrenes.

Preferably, in step i) a reaction mixture is obtained which contains at least 5 wt.-%, more preferably at least 10 wt.-% of at least one compound selected from the compounds of the formula (IV.a) and (IV.b), based on the total weight of the reaction mixture obtained in step i).

The yield of the compounds of the formula (IV.a) and (IV.b) in step i) is generally at least 60%, preferably at least 70% and particularly preferably at least 75%, based on the amount of the at least one compound of the formula (II) employed in step i).

The regioselectivity in step i) for the 1,6-disubstituted compounds of the formula (IV.a) and (IV.b) over the 1,2-, 1,3- and 1,4-disubstituted compounds is generally at least 55%, preferably at least 60% and particularly preferably at least 70%, based on the reacted amounts of the at least one compound of the formula (II) in step i).

In step ii) of the process of the invention, the reaction mixture obtained in step i) is subjected to a separation to obtain a fraction enriched with at least one compound selected from the compounds of the formula (IV.a) and (IV.b) and a fraction depleted with at least one compound selected from the compounds of the formula (IV.a) and (IV.b). Preferably, at least 70 wt.-%, more preferably at least 80 wt.-% and particularly preferably at least 90 wt.-% of the compounds of the formula (IV.a) and (IV.b), based on the total weight of the compounds of the formula (IV.a) and (IV.b) in the reaction mixture, are separated from the reaction mixture obtained in step i).

In the separation step ii), the compounds of the formula (IV.a) and (IV.b) are preferably separated from non-converted compounds of the formula (II) and (III), the transition metal catalyst, by-products and, if present, the solvent.

The separation of the compounds (IV.a) and (IV.b) in step ii) can principally be performed by all separation methods known to a person skilled in the art. Preferably, the compounds (IV.a) and (IV.b) are separated by distillation, crystallization, extraction, adsorption or a combination of these methods. Particularly preferably, the compounds (IV.a) and (IV.b) are separated by distillation. The distillation in step ii) can be performed by methods which are principally known to a person skilled in the art. Preferably, the distillation is performed in a vaporizer or in a distillation unit comprising a vaporizer and one or more distillation columns with trays or a packing.

Step iii) of the process of the invention is an optional step. In step iii) of the process of the invention, the fraction depleted with the at least one compound selected from the compounds of the formula (IV.a) and (IV.b) obtained in step ii) is optionally at least partially recycled to step i). The depleted fraction generally contains the by-products which are not completely hydroformylated unsaturated compounds, non-reacted alkanols of the formula (III) and the transition metal catalyst. The transition metal catalyst can generally be employed for further hydroformylations. It is particularly preferred to recycle the depleted fraction to step i) in the preferred embodiments in which the process is performed continuously or semicontinuously.

In step iv) of the process of the invention, the fraction enriched with at least one compound selected from the compounds of the formula (IV.a) and (IV.b) obtained in step ii) is subjected to a reaction in which the acetal groups are reacted to obtain the compound of the formula (I).

Preferably, the reaction in step iv) of the process of the invention in which the acetal groups in the compounds of the formula (IV.a) and (IV.b) are reacted is selected from hydrogenation reactions, oxidation reactions and amination reactions. The amination reaction in the sense of the invention is an amination reaction with an ammonia source.

In a preferred embodiment, the reaction in step iv) in which the acetal groups in the compounds of the formula (IV.a) and (IV.b) are reacted to obtain the compound of the formula (I) is a hydrogenation. In this case, both X in the compound of the formula (I) are $CH_2OH$. In this embodiment, the compound of the formula (I) is preferably 1,6-hexanediol.

The hydrogenation can principally be performed according to all processes known to a person skilled in the art which are suitable for the hydrogenation of aldehydes to alkanols.

Preferably, the hydrogenation in step iv) is performed in the presence of at least one hydrogenation catalyst. In principle, all catalysts can be employed which are known to a person skilled in the art for the hydrogenation of aldehydes to alkanols. The hydrogenation catalyst can be homogeneous or heterogeneous. Particularly preferred hydrogenation catalysts are those which are stable in the presence of water. Preferred hydrogenation catalysts comprise for example Co, Ni, Cu and mixtures thereof, in particular Ni.

Preferably, the hydrogenation in step iv) is performed in the presence of at least one acid. Principally suitable acids are Bronsted acids, Lewis acids and mixtures thereof. Particularly preferred are Bronsted acids. Preferred examples of suitable acids are trifluoroacetic acid, formic acid, hydrochloric acid, sulfuric acid, nitric acid, acidic pyridinium salts and p-toluenesulfonic acid. Also preferred are acidic ion exchangers, in particular sulfonated polystyrenes. In a preferred embodiment, the acid is an acidic material which is insoluble in the reaction mixture, preferably an acidic support material of a heterogeneous hydrogenation catalyst.

The hydrogenation in step iv) is preferably performed in the presence of water. Preferably the hydrogenation in step iv) is performed in the presence of 0.1 to 95 wt.-%, more preferably 0.5 to 30 wt.-% water, based on the total weight of the fraction enriched with at least one compound selected from the compounds of the formula (IV.a) and (IV.b). Further solvents may be present during the hydrogenation. Preferred are those solvents which are mentioned above as preferred for the hydroformylation of step i).

The hydrogenation in step iv) may be performed continuously, semicontinuously or discontinuously.

The hydrogenation reaction in step iv) can principally be performed in all reactors known by a person skilled in the art for this type of reaction. Suitable reactors are described for example in "Ullmanns Enzyklopädie der technischen Chemie", Vol. 1, 3rd edition, 1951, page 743 ff. Suitable pressure-resistant reactors are also known to a person skilled in the art and are described for example in "Ullmanns Enzyklopädie der technischen Chemie", Vol. 1, 3rd edition, 1951, page 769 ff. Preferably, for the hydrogenation in step iv) an autoclave is employed which may have an internal stirrer and an internal lining.

The temperature during the hydrogenation in step iv) is generally in the range from 20° C. to 180° C., more preferably in the range from 50° C. to 150° C.

The hydrogenation in step iv) is generally performed at the partial pressure of hydrogen at the respective reaction temperature. Preferably, the hydrogen pressure is in the range from 1 to 700 bar, more preferably from 1 to 600 bar and even more preferably from 1 to 300 bar. The hydrogen pressure can be adjusted depending on the activity of the employed hydrogenation catalyst.

Preferably, after the hydrogenation in step iv) the compound of the formula (I), preferably 1,6-hexanediol, is separated at least partially from the reaction mixture comprising the compound of the formula (I), non-converted compounds of the formula (II), non-converted alkanols of the formula (III), optionally the solvent and optionally water. The separation of the compound of the formula (I) can principally be performed by all separation methods known to a person skilled in the art. Preferably, the compound of the formula (I) is separated by distillation, crystallization, extraction, adsorption or a combination of these methods. Particularly preferably, the compound of the formula (I) is separated by distillation. The distillation can be performed by methods which are principally known to a person skilled in the art. Preferably, the distillation is performed in a vaporizer or in a distillation unit comprising a vaporizer and one or more distillation columns with trays or a packing.

Preferably, the reaction mixture obtained in the hydrogenation of step iv) is subjected to at least one separation step in order to separate at least partially at least one of the following components:
the at least one transition metal catalyst,
the non-converted at least one alkanol of the formula (III),
the non-converted at least one compound of the formula (II), reaction products different from the compounds of the formula (I), the solvent.

These components are separated by methods principally known to a person skilled in the art. Preferably, the at least one separation step is a distillation, crystallization, extraction, adsorption or a combination of these methods.

Preferably, at least one component selected from the non-converted at least one alkanol of the formula (III), the non-converted at least one compound of the formula (II) and the at least one transition metal catalyst is recycled to step i) of the process of the invention. The at least one transition metal catalyst can generally be employed for further hydroformylations.

The compound of the formula (I), in particular 1,6-hexanediol, is obtained in high yield, based on the compound of the formula (II), in particular butadiene.

In another preferred embodiment, the reaction in step iv) in which the acetal groups in the compounds of the formula (IV.a) and (IV.b) are reacted to obtain the compound of the formula (I) is an oxidation. In this case, both X in the compound of the formula (I) are COOH. In this embodiment, the compound of the formula (I) is preferably adipic acid.

The oxidation can principally be performed according to all processes known to a person skilled in the art which are suitable for the oxidation of aldehydes to carboxylic acids.

Preferably, the oxidation in step iv) is performed in the presence of at least one oxidation catalyst. In principle, all catalysts can be employed which are known to a person skilled in the art for the oxidation of aldehydes to carboxylic acids. The oxidation catalyst can be homogeneous or heterogeneous. Particularly preferred oxidation catalysts are those which are stable in the presence of water. Preferred oxidation catalysts are for example persulfates like peroxymonosulfates, in particular potassium peroxymonosulfate which is sold under the name Oxone® by Sigma-Aldrich.

Preferably, the oxidation in step iv) is performed in the presence of at least one acid. Principally suitable acids are Bronsted acids, Lewis acids and mixtures thereof. Particularly preferred are Bronsted acids. Preferred examples of suitable acids are trifluoroacetic acid, formic acid, hydrochloric acid, sulfuric acid, nitric acid, acidic pyridinium salts and p-toluenesulfonic acid. Also preferred are acidic ion exchangers, in particular sulfonated polystyrenes. In a preferred embodiment, the acid is an acidic material which is insoluble in the reaction mixture, preferably an acidic support material of a heterogeneous oxidation catalyst.

The oxidation in step iv) is preferably performed in the presence of water. Preferably, the oxidation in step iv) is performed in the presence of 0.1 to 95 wt.-%, more preferably 0.5 to 30 wt.-% water, based on the total weight of the fraction enriched with at least one compound selected from the compounds of the formula (IV.a) and (IV.b). Further solvents may be present during the oxidation. Preferred are those solvents which are mentioned above as preferred for the hydroformylation of step i).

The oxidation in step iv) may be performed continuously, semicontinuously or discontinuously.

The oxidation reaction in step iv) can principally be performed in all reactors known by a person skilled in the art for this type of reaction. Suitable reactors are described for example in "Ullmanns Enzyklopädie der technischen Chemie", Vol. 1, 3rd edition, 1951, page 743 ff. Suitable pressure-resistant reactors are also known to a person skilled in the art and are described for example in "Ullmanns Enzyklopädie der technischen Chemie", Vol. 1, 3rd edition, 1951, page 769 ff. Preferably, for the oxidation in step iv) an autoclave is employed which may have an internal stirrer and an internal lining.

The temperature during the oxidation in step iv) is generally in the range from 20° C. to 180° C., more preferably in the range from 50° C. to 150° C.

The oxidation in step iv) can principally be performed with any oxidant known to a person skilled in the art. The oxidant is preferably selected from oxygen gas, gas mixtures comprising oxygen gas and at least one inert gas, preferably air, hydrogen peroxide and mixtures thereof.

In a preferred embodiment, oxygen gas is employed as the oxidant. In this embodiment, the oxidation is generally performed at the partial pressure of oxygen at the respective reaction temperature. Preferably, the oxygen pressure is in the range from 0.1 to 40 bar, more preferably 0.5 to 10 bar.

Preferably, after the oxidation in step iv) the compound of the formula (I), preferably adipic acid, is separated at least partially from the reaction mixture comprising the compound of the formula (I), non-converted compounds of the formula (II), non-converted alkanols of the formula (III), optionally the solvent and optionally water. The separation of the compound of the formula (I) can principally be performed by all separation methods known to a person skilled in the art. Preferably, the compound of the formula (I) is separated by distillation, crystallization, extraction, adsorption or a combination of these methods. Particularly preferably, the compound of the formula (I) is separated by distillation. The distillation can be performed by methods which are principally known to a person skilled in the art. Preferably, the distillation is performed in a vaporizer or in a distillation unit comprising a vaporizer and one or more distillation columns with trays or a packing.

Preferably, the reaction mixture obtained in the oxidation of step iv) is subjected to at least one separation step in order to separate at least partially at least one of the following components:

the at least one transition metal catalyst, the non-converted at least one alkanol of the formula (III), the non-converted at least one compound of the formula (II), reaction products different from the compounds of the formula (I), the solvent.

These components are separated by methods principally known to a person skilled in the art. Preferably the at least one separation step is a distillation, crystallization, extraction, adsorption or a combination of these methods.

Preferably, at least one component selected from the non-converted at least one alkanol of the formula (III), the non-converted at least one compound of the formula (II) and the at least one transition metal catalyst is recycled to step i) of the process of the invention. The at least one transition metal catalyst can generally be employed for further hydroformylations.

The compound of the formula (I), in particular adipic acid, is obtained in high yield, based on the compound of the formula (II), in particular butadiene.

In another preferred embodiment, the reaction in step iv) in which the acetal groups in the compounds of the formula (IV.a) and (IV.b) are reacted to obtain the compound of the formula (I) is an amination with an ammonia source. In this case, both X in the compound of the formula (I) are $CH_2NH_2$. In this embodiment, the compound of the formula (I) is preferably 1,6-hexanediamine.

The amination can principally be performed according to all processes known to a person skilled in the art which are suitable for the reaction of aldehydes with an ammonia source, preferably ammonia, to obtain amines.

Preferably, the amination in step iv) is performed in the presence of at least one amination catalyst. In principle, all catalysts can be employed which are known to a person skilled in the art for the amination of aldehydes with an ammonia source, preferably ammonia, to obtain amines. The amination catalyst can be homogeneous or heterogeneous. Particularly preferred amination catalysts are those which are stable in the presence of water. Preferred amination catalysts comprise Co, Ni, Cu or mixtures thereof, in particular Ni.

Preferably, the amination in step iv) is performed in the presence of at least one acid. Principally suitable acids are Bronsted acids, Lewis acids and mixtures thereof. Particularly preferred are Bronsted acids. Preferably, the acid is employed is the form of an ammonium salt which forms an acid under the reaction conditions of the amination. Particularly preferred are ammonium acetate, ammonium chloride, ammonium bromide, ammonium formiate and mixtures thereof. In a preferred embodiment, the acid is an acidic material which is insoluble in the reaction mixture, preferably an acidic support material of a heterogeneous amination catalyst.

The amination in step iv) is preferably performed in the presence of water. Preferably, the amination in step iv) is performed in the presence of 0.1 to 95 wt.-%, more preferably 0.5 to 30 wt.-% water, based on the total weight of the fraction enriched with at least one compound selected from the compounds of the formula (IV.a) and (IV.b). Further solvents may be present during the amination. Preferred are those solvents which are mentioned above as preferred for the hydroformylation of step i).

The amination in step iv) may be performed continuously, semicontinuously or discontinuously.

The amination reaction in step iv) can principally be performed in all reactors known by a person skilled in the art for this type of reaction. Suitable reactors are described for example in "Ullmanns Enzyklopädie der technischen Chemie", Vol. 1, 3rd edition, 1951, page 743 ff. Suitable pressure-resistant reactors are also known to a person skilled in the art and are described for example in "Ullmanns Enzyklopädie der technischen Chemie", Vol. 1, 3rd edition, 1951, page 769 ff. Preferably, for the amination in step iv) an autoclave is employed which may have an internal stirrer and an internal lining.

The temperature during the amination in step iv) is generally in the range from 20° C. to 300° C., more preferably in the range from 50° C. to 200° C.

Preferred ammonia sources for the amination of step iv) are ammonia, in particular gaseous ammonia and aqueous ammonia solutions, or ammonium salts.

In a preferred embodiment, gaseous ammonia is employed. In this embodiment, the amination in step iv) is generally performed at the partial pressure of ammonia at the respective reaction temperature. Preferably, the ammonia pressure is in the range from 1 to 700 bar, more preferably from 1 to 600 bar and even more preferably from 1 to 300 bar. The ammonia pressure can be adjusted depending on the activity of the employed amination catalyst.

Preferably, after the amination in step iv) the compound of the formula (I), preferably 1,6-hexanediamine, is separated at least partially from the reaction mixture comprising the compound of the formula (I), non-converted compounds of the formula (II), non-converted alkanols of the formula (III), optionally the solvent and optionally water. The separation of the compound of the formula (I) can principally be performed by all separation methods known to a person skilled in the art. Preferably, the compound of the formula (I) is separated by distillation, crystallization, extraction, adsorption or a combination of these methods. Particularly preferably, the compound of the formula (I) is separated by distillation. The distillation can be performed by methods which are principally known to a person skilled in the art. Preferably, the distillation is performed in a vaporizer or in a distillation unit comprising a vaporizer and one or more distillation columns with trays or a packing.

Preferably, the reaction mixture obtained in the amination of step iv) is subjected to at least one separation step in order to separate at least partially at least one of the following components:

the at least one transition metal catalyst,
the non-converted at least one alkanol of the formula (III),
the non-converted at least one compound of the formula (II),
reaction products different from the compounds of the formula (I),
the solvent.

These components are separated by methods principally known to a person skilled in the art. Preferably the at least one separation step is a distillation, crystallization, extraction, adsorption or a combination of these methods.

Preferably, at least one component selected from the non-converted at least one alkanol of the formula (III), the non-converted at least one compound of the formula (II) and the at least one transition metal catalyst is recycled to step i) of the process of the invention. The at least one transition metal catalyst can generally be employed for further hydroformylations.

The compound of the formula (I), in particular 1,6-hexanediamine, is obtained in high yield, based on the compound of the formula (II), in particular butadiene.

The invention also relates to a process for the production of polyamide 6.6, wherein butadiene is aminated in the process of the invention described above to obtain 1,6-hexanediamine and wherein the obtained 1,6-hexanediamine is reacted with adipic acid to obtain the polyamide 6.6. The adipic acid employed in this process may also be produced by the process of the invention.

Processes for the production of polyamide 6.6 from 1,6-hexanediamine and adipic acid are principally known to a person skilled in the art. Polyamide 6.6 is prepared predominantly by polycondensation of what are called AH salt solutions, i.e. aqueous solutions comprising adipic acid and 1,6-hexanediamine in stoichiometric amounts. Conventional preparation processes for polyamide 6.6 are described, for example, in Kunststoffhandbuch, 3/4 Technische Thermoplaste: Polyamide [Plastics Handbook, 3/4 Industrial Thermoplastics: Polyamides], Carl Hanser Verlag, 1998, Munich, p. 42-71.

The invention is described in more detail in the following examples.

EXAMPLES

Employed Materials
acetic acid (laboratory reagent grade, Fischer Scientific)
benzene (anhydrous, 99.8%, Sigma-Aldrich)
butadiene (2.25 M in toluene) (Sigma-Aldrich)
diethyl ether (>99.5%, 7 ppm BHT, Bernd Kraft)
1,2-ethanediol (anhydrous, 99.8%, Sigma Aldrich)
ethyl acetate (>99.5%, Sigma-Aldrich)
kieselguhr (Acros Organics)
methanol (>99.6%, Sigma-Aldrich)

n-nonane (anhydrous, >99%, Sigma-Aldrich)
Oxone® (KHSO$_5$.0.5 KHSO$_4$.0.5 K$_2$SO$_4$) (Sigma-Aldrich)
Raney® nickel (Sigma-Aldrich)
rhodiumbiscarbonylacetylacetonate ([Rh(acac)(CO)$_2$]) (98%, Sigma Aldrich)
sodium carbonate (>99.5%, Sigma-Aldrich)
sulfuric acid (96% in water, Acros Organics)
tartaric acid (DL, 99%, Sigma-Aldrich)
toluene (anhydrous, 99.8%, Sigma-Aldrich)
trifluoroacetic acid (0.14 M in toluene) (99.5%, Acros Organics, diluted with toluene)
water
tMe-Rucaphosphite (Compound (V.a)) (Synthesized)

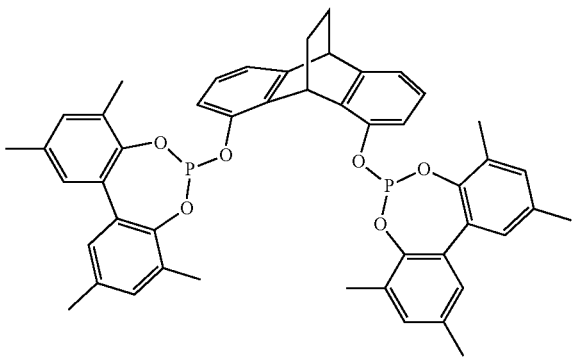

(V.a)

Biphephos (Compound (V.b)) (97%, Sigma-Aldrich)

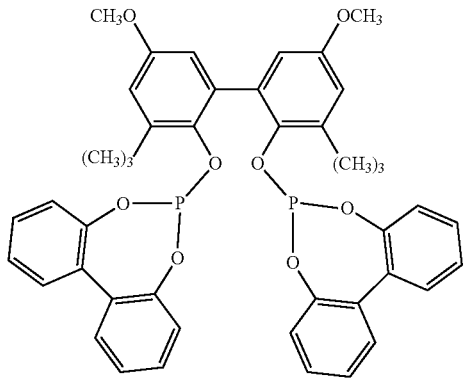

(V.b)

Analytics

Gas Chromatography (GC)

The employed gas chromatograph was an Agilent Technologies 6890N Network GC System equipped with a 30 m HP-5 column ((5%-Phenyl)-methylpolysiloxane). The He flow rate was kept at 2.0 mL/min. The column temperature was initially held at 40° C. for 1 min, then ramped at 4° C./min to 90° C., followed by an immediate temperature ramp of 30° C./min to 200° C., held at this temperature for 5 min, followed by a temperature ramp of 20° C./min to 250° C. and held at this temperature for 5 min. In the examples the obtained reaction mixtures were examined by means of gas chromatography without further purification. n-Nonane was employed as internal standard. The area under each signal was determined. The ratio of the di-acetal of 1,6-hexanedial to the di-acetals of 1,2-, 1,3- and 1,4-hexanedial was determined in the obtained reaction mixtures to account for inaccuracies in the addition of the compound of the formula (II) and n-nonane.

Gas Chromatography Coupled with Mass Spectrometry (GC-MS)

GC-MS analysis was performed on an Agilent Technologies 5975B (inert MSD) System equipped with a 30 m HP-5MS column. The He flow rate and the temperature program was the same as for the GC analysis.

NMR Spectroscopy

NMR analysis was performed using a Bruker DPX-200 MHz spectrometer.

Preparation of the Compounds of the Formula (IV.a) and (IV.b) (Step i) of the Process of the Invention)

General Procedure 45 mg of tMe-Rucaphosphite (compound (V.a)) or Biphephos (compound (V.b)), 5 mg rhodiumbiscarbonylacetylacetonate and 25 µL n-nonane as internal standard were dissolved in 5 mL toluene under an atmosphere of an inert gas in a glovebox and transferred into an autoclave made of steel which had a volume of 25 mL and an internal stirrer. The autoclave was purged several times with a gas mixture of carbon monoxide and hydrogen which had a volume ratio of carbon monoxide to hydrogen of 1:1. The autoclave was filled with the gas mixture of carbon monoxide and hydrogen to a pressure of 15 bar. The autoclave was heated to 100° by means of an oil bath (heating rate about 10° C./min), stirred at this temperature for one hour and cooled to 0° C. by means of an ice bath. 1 mL butadiene solution (2.25 M in toluene), 1 mL 1,2-ethanediol and 0.05 mL trifluoroacetic acid solution (0.14 M in toluene) were added to the reaction mixture during a weak counter flow of the gas mixture of carbon monoxide and hydrogen. The autoclave was filled with the gas mixture of carbon monoxide and hydrogen to a pressure of 30 bar and the reaction mixture was subjected to the conditions described in the examples below.

Example 1

The example was performed according to the general procedure described above. tMe-Rucaphosphite (compound (V.a)) was employed. The autoclave was heated to 80° C. and the reaction mixture was stirred at this temperature for 2 hours. The temperature was increased to 120° C. and the reaction mixture was stirred at this temperature for 18 hours. Afterwards, the gaschromatographic analysis showed 63% di-acetal of 1,6-hexanedial, 16% di-acetals of 1,2-, 1,3- and 1,4-hexanedial, 14% acetal of pentanal, 6% acetal of 3-pentenal and small amounts of other products. The ratio of the di-acetal of 1,6-hexanedial to the di-acetals of 1,2-, 1,3- and 1,4-hexanedial was 3.9.

Example 2

The example was performed according to example 1, except that Biphephos (compound (V.b)) was employed instead of tMe-Rucaphosphite (compound (V.a)). Afterwards, the gaschromatographic analysis showed 65% di-acetal of 1,6-hexanedial, 9% di-acetals of 1,2-, 1,3- and 1,4-hexanedial, 31% acetal of pentanal and small amounts of other products. The ratio of the di-acetal of 1,6-hexanedial to the di-acetals of 1,2-, 1,3- and 1,4-hexanedial was 7.2.

Example 3

The example was performed according to the general procedure described above. tMe-Rucaphosphite (compound (V.a)) was employed. The autoclave was heated to 80° C. and the reaction mixture was stirred at this temperature for 2 hours. The autoclave was cooled to 0° C. by means of an ice bath and the pressure in the autoclave was reduced to 10 bar. The autoclave was heated to 120° C. and the reaction mixture was stirred at this temperature for 18 hours. Afterwards, the gaschromatographic analysis showed 73% di-acetal of 1,6-hexanedial, 12% di-acetals of 1,2-, 1,3- and 1,4-hexanedial, 19% acetal of pentanal and small amounts of other products. The ratio of the di-acetal of 1,6-hexanedial to the di-acetals of 1,2-, 1,3- and 1,4-hexanedial was 6.1.

Example 4

The example was performed according to example 3, except that acetic acid was employed instead of trifluoroacetic acid solution. Afterwards, the gaschromatographic analysis showed 65% di-acetal of 1,6-hexanedial, 12% di-acetals of 1,2-, 1,3- and 1,4-hexanedial, 18% acetal of pentanal and small amounts of other products. The ratio of the di-acetal of 1,6-hexanedial to the di-acetals of 1,2-, 1,3- and 1,4-hexanedial was 5.4.

Example 5

The example was performed according to example 3, except that no trifluoroacetic acid solution was added. Afterwards, the gaschromatographic analysis showed 65% di-acetal of 1,6-hexanedial, 12% di-acetals of 1,2-, 1,3- and 1,4-hexanedial, 21% acetal of pentanal and small amounts of other products. The ratio of the di-acetal of 1,6-hexanedial to the di-acetals of 1,2-, 1,3- and 1,4-hexanedial was 5.4.

Comparative Example 1

The example was performed according to the general procedure described above. tMe-Rucaphosphite (compound (V.a)) was employed. The autoclave was heated to 80° C. and the reaction mixture was stirred at this temperature for 20 hours. Afterwards, the gaschromatographic analysis showed 39% di-acetal of 1,6-hexanedial, 6% di-acetals of 1,2-, 1,3- and 1,4-hexanedial, 2% acetal of pentanal, 61% acetal of 3-pentenal and small amounts of other products. The ratio of the di-acetal of the 1,6-hexanedial to the di-acetals of 1,2-, 1,3- and 1,4-hexanedial was 6.5.

Comparative Example 2

The example was performed according to the general procedure described above. Biphephos (compound (V.b)) was employed. The autoclave was heated to 120° C. and the reaction mixture was stirred at this temperature for 20 hours. Afterwards, the gaschromatographic analysis showed 52% di-acetal of 1,6-hexanedial, 8% di-acetals of 1,2-, 1,3- and 1,4-hexanedial, 44% acetal of pentanal and small amounts of other products. The ratio of the di-acetal of 1,6-hexanedial to the di-acetals of 1,2-, 1,3- and 1,4-hexanedial was 6.5.

Preparation of the Compounds of the Formula (I) (Steps ii), iii) and iv) of the Process of the Invention)

Example 6

90 mg tMe-Rucaphosphite (compound (V.a)), 10 mg rhodiumbiscarbonylacetylacetonate and 50 μL n-nonane as internal standard were dissolved in 10 mL benzene under an atmosphere of an inert gas in a glovebox and transferred into an autoclave made of steel which had a volume of 25 mL and an internal stirrer. The autoclave was purged several times with a gas mixture of carbon monoxide and hydrogen which had a volume ratio of carbon monoxide to hydrogen of 1:1. The autoclave was filled with the gas mixture of carbon monoxide and hydrogen to a pressure of 15 bar. The autoclave was heated to 100° C., stirred at this temperature for one hour and cooled to 0° C. by means of an ice bath. 2 mL butadiene solution (2.25 M in toluene), 2 mL 1,2-ethanediol and 0.1 mL trifluoroacetic acid solution (0.14 M in toluene) were added to the reaction mixture during a weak counter flow of the gas mixture of carbon monoxide and hydrogen. The autoclave was filled with the gas mixture of carbon monoxide and hydrogen to a pressure of 30 bar. The autoclave was heated to 80° C. and the reaction mixture was stirred at this temperature for 2 hours. The autoclave was cooled to 0° C. by means of an ice bath and the pressure in the autoclave was reduced to 10 bar. The autoclave was heated to 120° C. and the reaction mixture was stirred at this temperature for 18 hours. After cooling down, the reaction mixture was diluted with 10 mL of benzene, washed with 10 mL of a saturated NaHCO$_3$ solution and filtered over a short plug of silica. The solvent was removed under reduced pressure. 4 mL water and 0.1 mL sulfuric acid were added to the residue which was then stirred for 15 minutes. 1 g Oxone® was added and the mixture was stirred for 3 hours. Another 0.5 g Oxone® was added and the mixture was stirred for 16 hours. Another 0.25 g Oxone® were added and the mixture was stirred for 3 hours. The mixture was extracted four times with in each case 10 mL ethyl acetate and the solvent was removed under reduced pressure to give 0.5 g of an off-white powder. Analysis with NMR spectroscopy showed that the product mixture contained >70% adipic acid.

Example 7

The di-acetal of 1,6-hexanedial was synthesized starting from 1,2-cyclohexanediol. The di-acetal was formed from 1,2-ethanediol in benzene. The procedure is described in X.-X. Deng, Y. Cui, F.-S. Du, Z.-C. Li, Polym. Chem. 2014, 5, 3316-3320 and T.-J. Lu, J.-F. Yang, L.-J. Sheu, J. Org. Chem. 1995, 60, 2931-2934.

1 g di-acetal of 1,6-hexanedial was mixed with 10 mL water and 0.05 mL trifluoroacetic acid solution (0.14 M in toluene) in an autoclave made of steel with an internal stirrer. 10 mL methanol and 2 g of an aqueous suspension of Raney® nickel in water (80 wt.-%) were added to the reaction mixture. The autoclave was filled with hydrogen to a pressure of 40 bar. The autoclave was heated to 120° C., stirred at this temperature for 3 hours and allowed to cool to room temperature. The Raney® nickel was separated from the reaction mixture via filtration over kieselguhr. The solvent was removed under reduced pressure which afforded 1 g of a product mixture. Analysis with gas chromatography showed that the product mixture contained 15 mol-% 1,6-hexanediol and 61 mol-% non-converted di-acetal of 1,6-hexanedial.

Example 8

The di-acetal of 1,6-hexanedial was synthesized starting from 1,2-cyclohexanediol. The di-acetal was formed from 1,2-ethanediol in benzene. The procedure is described in X.-X. Deng, Y. Cui, F.-S. Du, Z.-C. Li, Polym. Chem. 2014, 5, 3316-3320 and T.-J. Lu, J.-F. Yang, L.-J. Sheu, J. Org. Chem. 1995, 60, 2931-2934.

0.1 g di-acetal of 1,6-hexanedial, 1 g ammonium acetate, 3 mL acetic acid, 3 mL water, 6 mL methanol and 0.5 g of an aqueous suspension of Raney® nickel in water (80 wt.-%) were mixed in an autoclave made of steel with an internal stirrer. The autoclave was heated to 130° C., stirred at this temperature for 2 hours and allowed to cool to room temperature. The autoclave was filled with hydrogen to a pressure of 30 bar, heated to 130° C. and stirred at this temperature for 2 hours. The autoclave was allowed to cool to room temperature and 2.0 g sodium carbonate were added to the reaction mixture. The reaction mixture was extracted twice with 5 mL diethyl ether. Analysis of the diethyl ether solution with gas chromatography coupled with mass spectrometry (GC-MS) showed only one signal which can be attributed to azepane.

The invention claimed is:
1. A process for the production of a compound of the formula (I)

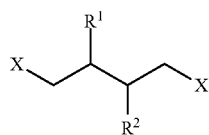

(I)

wherein
X are both $CH_2NH_2$, $CH_2OH$ or COOH,
$R^1$ and $R^2$ are independently from each other hydrogen or linear or branched $C_1$-$C_4$-alkyl,
comprising the following steps:
i) subjecting at least one compound of the formula (II)

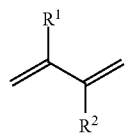

(II)

wherein $R^1$ and $R^2$ have the same meaning as in formula (I),
to a hydroformylation with carbon monoxide and hydrogen in the presence of at least one transition metal catalyst,
wherein the hydroformylation is performed in the presence of at least one alkanol of the formula (III)

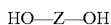

HO—Z—OH  (III)

wherein
Z is a hydrocarbon chain having 2 or 3 carbon atoms which is unsubstituted or substituted and which may be part of a carbocycle, a heterocycle or an aromatic or heteroaromatic ring,
wherein during the hydroformylation the temperature is increased for at least 10° C. from a temperature $T_1$ to a temperature $T_2$,
to obtain a reaction mixture comprising at least one compound selected from the compounds of the formula (IV.a) and (IV.b),

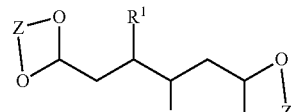

(IV.a)

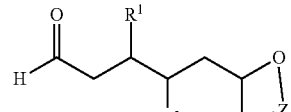

(IV.b)

wherein
Z has the same meaning as in formula (III), and
$R^1$ and $R^2$ have the same meaning as in formula (I),
ii) subjecting the reaction mixture obtained in step i) to a separation to obtain a fraction enriched with at least one compound selected from the compounds of the formula (IV.a) and (IV.b) and a fraction depleted with at least one compound selected from the compounds of the formula (IV.a) and (IV.b),
iii) optionally recycling at least partially the fraction depleted with at least one compound selected from the compounds of the formula (IV.a) and (IV.b) obtained in step ii) to step i), and
iv) subjecting the fraction enriched with at least one compound selected from the compounds of the formula (IV.a) and (IV.b) obtained in step ii) to a reaction in which the acetal groups in the compounds of the formula (IV.a) and (IV.b) are reacted to obtain the compound of the formula (I).

2. The process according to claim 1, wherein the at least one compound of the formula (II) is butadiene.

3. The process according to claim 1, wherein the temperature is increased from $T_1$ to $T_2$ after at least 50 mol-% of the double bond equivalents of the at least one compound of the formula (II) are reacted.

4. The process according to claim 1, wherein $T_1$ is at least 40° C.

5. The process according to claim 1, wherein $T_2$ is at least 110° C.

6. The process according to claim 1, wherein $T_1$ is in the range from 40 to 100° C. and $T_2$ is in the range from 110 to 150° C.

7. The process according to claim 1, wherein in step i) the pressure is decreased.

8. The process according to claim 1, wherein the molar ratio of the at least one compound of the formula (II) to the at least one alkanol of the formula (III) is in the range from 1:1 to 1:100.

9. The process according to claim 1, wherein step i) is performed in the presence of at least one acid.

10. The process according to claim 1, wherein the at least one transition metal catalyst comprises at least one transition metal selected from Co, Ru, Ir, Rh, Ni, Pd and Pt.

11. The process according to claim 9, wherein the at least one transition metal catalyst comprises at least one bidentate ligand which is bound over two P atoms to a transition metal and wherein the bidentate ligand has a natural bite-angle in the range from 90° to 1300.

12. The process according to claim 1, wherein the at least one transition metal catalyst comprises at least one ligand of the formula (V)

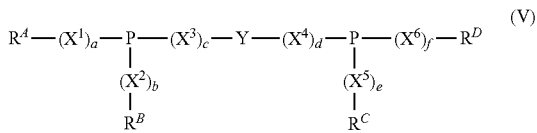

wherein
$R^A$, $R^B$, $R^C$ and $R^D$ are independently from each other alkyl, cycloalkyl, heterocycloalkyl, aryl or hetaryl, wherein the alkyl radicals may carry 1, 2, 3, 4 or 5 substituents selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, carboxyl, $SO_3H$, sulfonate, $NE^1E^2$, $NE^1E^2E^{3+}X^-$, halogen, nitro, formyl, acyl and cyano, wherein $E^1$, $E^2$ and $E^3$ are the same or different and are selected from hydrogen, alkyl, cycloalkyl, and aryl and $X^-$ is an anion equivalent, and wherein the radicals cycloalkyl, heterocycloalkyl, aryl and hetaryl $R^A$, $R^B$, $R^C$ and $R^D$ may carry 1, 2, 3, 4 or 5 substituents selected from alkyl and the substituents mentioned for the alkyl radicals $R^A$, $R^B$, $R^C$ and $R^D$ before, or $R^A$ and $R^B$ and/or $R^C$ and $R^D$ together with the P atom and, if present, the groups $X^1$, $X^2$, $X^5$ and $X^6$ to which they are bound, are a 5- to 8-membered heterocycle which is optionally fused with one, two or three groups selected from cycloalkyl, heterocycloalkyl, aryl and heteroaryl, wherein the heterocycle and, if present, the fused-on groups independently from each other may each carry 1, 2, 3 or 4 substituents selected from alkyl, cycloalkyl, heterocycloalkyl, aryl, hetaryl, hydroxy, mercapto, polyalkylene oxide, polyalkyleneimine, alkoxy, halogen, carboxyl, $SO_3H$, sulfonate, $NE^4E^5$, $NE^4E^5E^{6+}X^-$, nitro, alkoxycarbonyl, formyl, acyl and cyano, wherein $E^4$, $E^5$ and $E^6$ are the same or different and are selected from hydrogen, alkyl, cycloalkyl and aryl and $X^-$ is an anion equivalent, $X^1$, $X^2$, $X^3$, $X^4$, $X^5$ and $X^6$ are independently from each other O, S, $SiR^xR^y$ or $NR^z$, wherein $R^x$, $R^y$ and $R^z$ are independently from each other hydrogen, alkyl, cycloalkyl, heterocycloalkyl, aryl or hetaryl, Y is a divalent bridging group which contains carbon atoms, and a, b, c, d, e and f are independently from each other 0 or 1.

13. The process according to claim 1, wherein the at least one transition metal catalyst comprises at least one ligand of the formula (V.1)

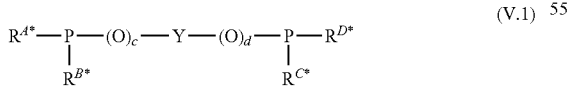

Wherein
Y is a divalent bridging group which contains carbon atoms,
c and d are independently from each other 0 or 1, and
the radicals $R^{A*}$, $R^{B*}$, $R^{C*}$ and $R^{D*}$ are independently from each other selected from the groups of the formula (VI.a) to (VI.k)

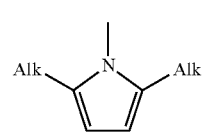

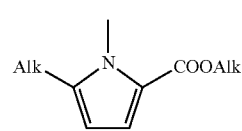

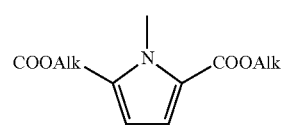

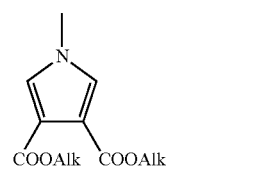

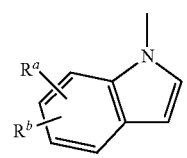

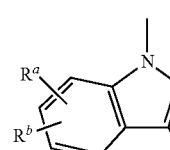

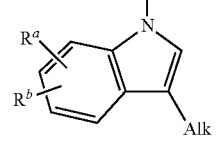

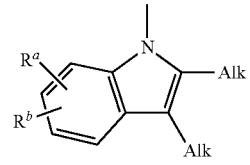

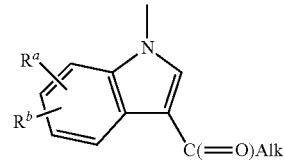

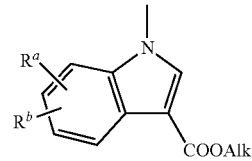

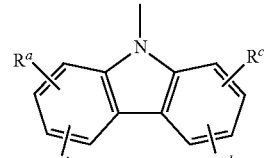

wherein

Alk is a $C_1$-$C_4$-alkyl group, and $R^a$, $R^b$, $R^c$ and $R^d$ are independently from each other hydrogen, $C_1$-$C_4$-alkyl, $C_1$-$C_4$-alkoxy, formyl, acyl, halogen, $C_1$-$C_4$-alkoxycarbonyl or carboxyl.

14. The process according to claim 1, wherein the at least one transition metal catalyst comprises at least one ligand of the formula (VII)

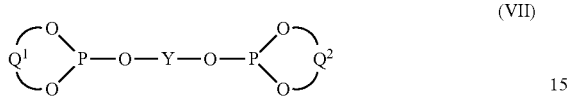

(VII)

wherein

Y is a divalent bridging group which contains carbon atoms, $Q^1$ and $Q^2$ are independently from each other a divalent bridging group of the formula (VIII),

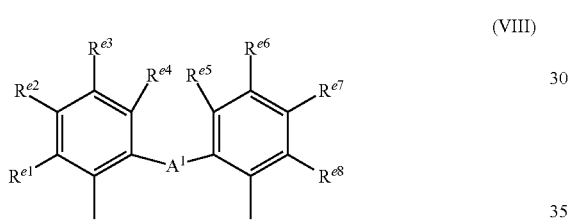

(VIII)

Wherein $R^{e1}$, $R^{e2}$, $R^{e3}$, $R^{e4}$, $R^{e5}$, $R^{e6}$, $R^{e7}$ and $R^{e8}$ are independently from each other hydrogen, in each case unsubstituted or substituted alkyl, alkoxy, cycloalkyl, cycloalkoxy, heterocycloalkyl, heterocycloalkoxy, aryl, aryloxy, hetaryl, hetaryloxy, halogen, hydroxy, mercapto, cyano, nitro, formyl, acyl, carboxy, carboxylate, alkylcarbonyloxy, carbamoyl, $SO_3H$, sulfonate or $NE^{12}E^{13}$, wherein $E^{12}$ and $E^{13}$ are the same or different and are selected from hydrogen, alkyl, cycloalkyl, heterocycloalkyl, aryl and hetaryl, wherein two adjacent radicals $R^{e1}$ to $R^{e8}$ together with the carbon atoms of the benzene ring to which they are bound may also be a condensed ring system with 1, 2 or 3 further rings, and $A^1$ is a single bond, O, S, $NR^{a31}$, $SiR^{a32}R^{a33}$ or $C_1$-$C_4$-alkylene, which may have a double bond and/or which may be substituted with alkyl, cycloalkyl, heterocycloalkyl, aryl or hetaryl or which may be interrupted by O, S, $NR^{31}$ or $SiR^{a32}R^{a33}$, wherein $R^{a31}$, $R^{a32}$ and $R^{a33}$ are independently from each other hydrogen, alkyl, cycloalkyl, heterocycloalkyl, aryl or hetaryl.

15. The process according to claim 12, wherein the divalent bridging group Y is selected from the groups of the formula (IX.a) to (IX.u)

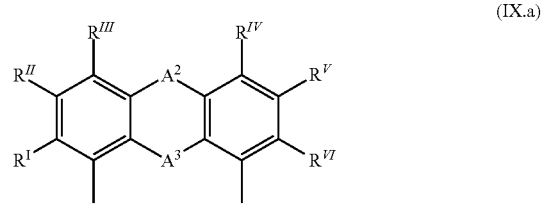

(IX.a)

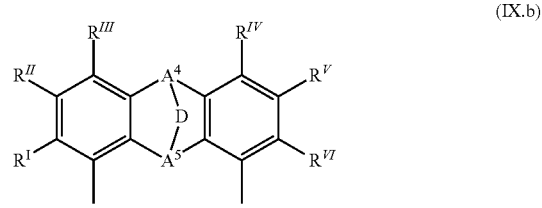

(IX.b)

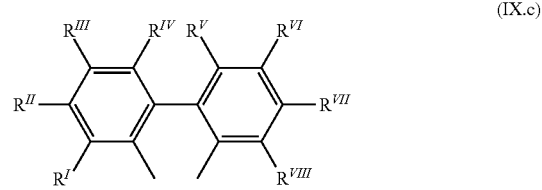

(IX.c)

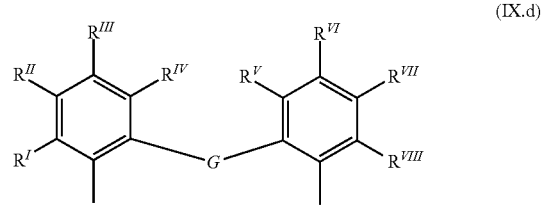

(IX.d)

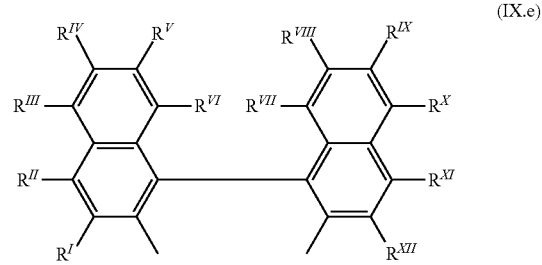

(IX.e)

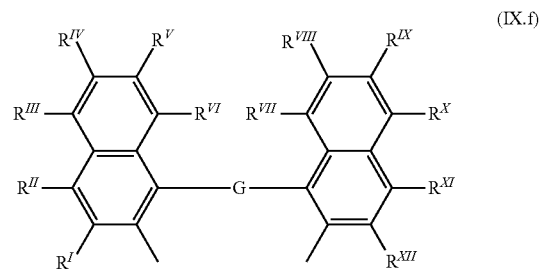

(IX.f)

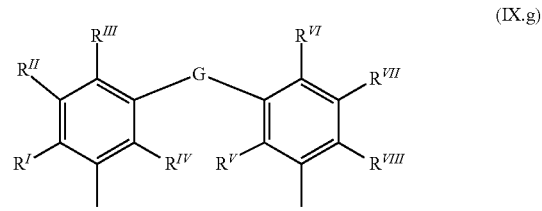

(IX.g)

-continued (IX.h) 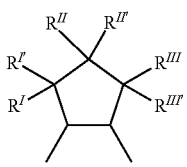

(IX.i) 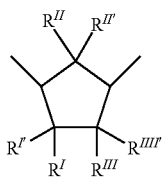

(IX.k) 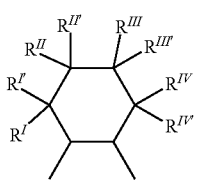

(IX.l) 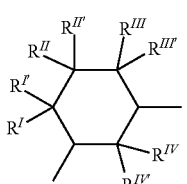

(IX.m) 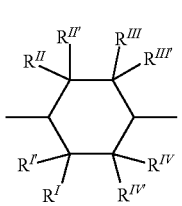

(IX.n) 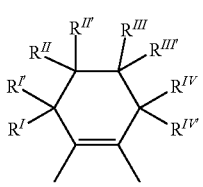

(IX.o) 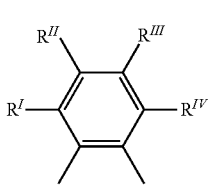

(IX.p) 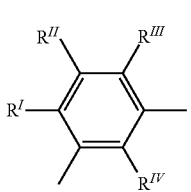

-continued (IX.q) 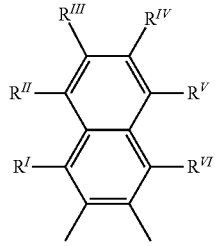

(IX.r) 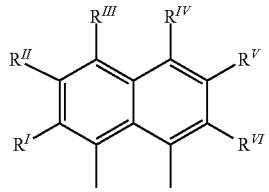

(IX.s) 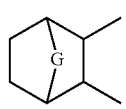

(IX.t) 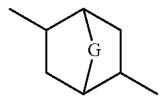

(IX.u) 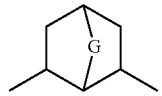

wherein $R^I$, $R^{I'}$, $R^{II}$, $R^{II'}$, $R^{III}$, $R^{III'}$, $R^{IV}$, $R^{IV'}$, $R^V$, $R^{VI}$, $R^{VII}$, $R^{VIII}$, $R^{IX}$, $R^X$, $R^{XI}$ and $R^{XII}$ are each, independently from each other, hydrogen, alkyl, cycloalkyl, heterocycloalkyl, aryl, hetaryl, hydroxy, thiol, polyalkylene oxide, polyalkylenimine, alkoxy, halogen, $SO_3H$, sulfonate, $NE^1E^2$, alkylene-$NE^1E^2$, nitro, alkoxycarbonyl, carboxyl, acyl or cyano, wherein $E^1$ and $E^2$ are identical or different and are selected from hydrogen, alkyl, cycloalkyl and aryl, G is O, S, $NR^\delta$ or $SiR^\delta R^\epsilon$, wherein $R^\delta$ and $R^\epsilon$ are each, independently from each other, hydrogen, alkyl, cycloalkyl, heterocycloalkyl, aryl or hetaryl, or G is a $C_1$-$C_4$-alkylene bridge which may have a double bond and/or which carries an alkyl, cycloalkyl, heterocycloalkyl, aryl or hetaryl substituent, or G is a $C_2$-$C_4$-alkylene bridge which is interrupted by O, S or $NR^\delta$ or $SiR^\delta R^\epsilon$, wherein in the groups of the formula (IX.a) and (IX.b), two adjacent radicals $R^I$ to $R^{VI}$ together with the carbon atoms of the benzene ring to which they are bound may also form a fused ring system having 1, 2 or 3 further rings, wherein in the groups of the formula (IX.h) to (IX.n), two geminal radicals $R^I$, $R^{I'}$; $R^{II}$, $R^{II'}$; $R^{III}$, $R^{III'}$ and/or $R^{IV}$, $R^{IV'}$ may also represent oxo or a ketal thereof, $A^2$ and $A^3$ are each, independently from each other, O, S, $SiR^\Phi R^\gamma$, $NR^\eta$ or $CR^\iota R^\kappa$, wherein $R^\Phi$, $R^\gamma$, $R^\eta$, $R^\iota$ and $R^\kappa$ are each, independently from each other, hydrogen, alkyl, cycloalkyl, heterocycloalkyl, aryl or hetaryl, $A^4$ and $A^5$ are each, independently from each other, $SiR^\Phi$, N or $CR^\iota$, ι

D is a divalent bridging group of the formula

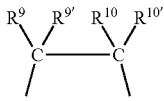

Wherein $R^9$, $R^{9'}$, $R^{10}$ and $R^{10'}$ are each, independently from each other, hydrogen, alkyl, cycloalkyl, aryl, halogen, trifluoromethyl, carboxyl, carboxylate or cyano, wherein $R^{9'}$ together with $R^{10'}$ may also represent the second bond of a double bond between the two carbon atoms to which $R^{9'}$ and $R^{10'}$ are bound, and/or $R^9$ and $R^{10}$ together with the carbon atoms to which they are bound may also form a 4- to 8-membered carbocycle or heterocycle which may additionally be fused with one, two or three cycloalkyl, heterocycloalkyl, aryl or hetaryl groups, wherein the heterocycle and, if present, the fused-on groups may each carry, independently from each other, 1, 2, 3 or 4 substituents selected from alkyl, cycloalkyl, heterocycloalkyl, aryl, hetaryl, $COOR^f$, $COO^-M^+$, $SO_3R$, $SO_3^-M^+$, $NE^4E^5$, alkylene-$NE^4E^5$, $NE^4E^5E^{6+}X^-$, alkylene-$NE^4E^5E^{6+}X^-$, $OR^f$, $SR^f$, $(CHR^eCH_2O)_yR^f$, $(CH_2N(E^4))_yR^f$, $(CH_2CH_2N(E^4))_yR^f$, halogen, trifluoromethyl, nitro, acyl and cyano, wherein $R^f$, $E^4$, $E^5$ and $E^6$ are the same or different and are selected from hydrogen, alkyl, cycloalkyl and aryl, $R^e$ is hydrogen, methyl or ethyl, $M^+$ is a cation equivalent, $X^-$ is an anion equivalent, and y is an integer from 1 to 240.

16. The process according to claim 1, wherein the at least one transition metal catalyst comprises at least one ligand selected from the compounds of the formula (V.a) and (V.b)

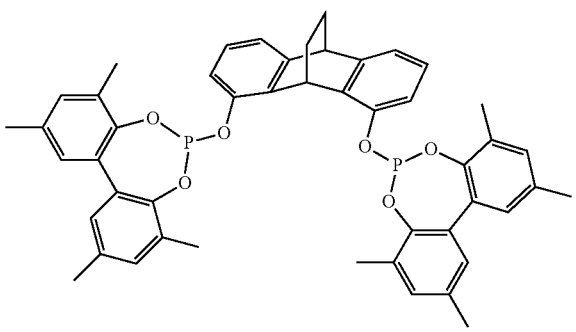

(V.a)

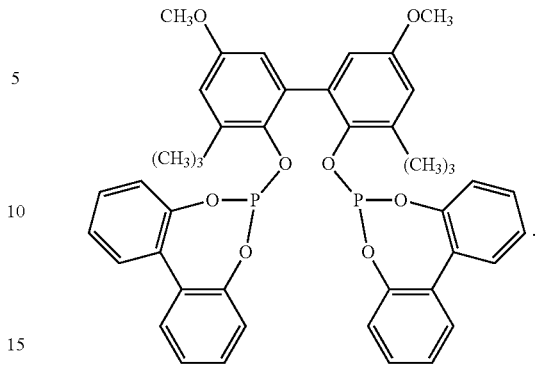

(V.b)

17. The process according to claim 1, wherein the reaction in step iv) is a hydrogenation and both X in the compound of the formula (I) are $CH_2OH$.

18. The process according to claim 17, wherein the hydrogenation in step iv) is performed in the presence of at least one hydrogenation catalyst selected from Co, Ni, Cu and mixtures thereof.

19. The process according to claim 17, wherein the hydrogenation in step iv) is performed in the presence of at least one acid.

20. The process according to claim 1, wherein the reaction in step iv) is an oxidation and both X in the compound of the formula (I) are COOH.

21. The process according to claim 20, wherein the oxidation in step iv) is performed in the presence of at least one oxidation catalyst.

22. The process according to claim 20, wherein the oxidation in step iv) is performed in the presence of at least one acid.

23. The process according to claim 1, wherein the reaction performed in step iv) is an amination with an ammonia source and both X in the compound of the formula (I) are $CH_2NH_2$.

24. The process according to claim 23, wherein the amination in step iv) is performed in the presence of at least one amination catalyst selected from Co, Ni, Cu and mixtures thereof.

25. The process according to claim 23, wherein the amination in step iv) is performed in the presence of at least one acid.

26. The process according to claim 1, wherein the reaction in step iv) is performed in the presence of 0.5 to 30 wt.-% water, based on the total weight of the fraction enriched with at least one compound selected from the compounds of the formula (IV.a) and (IV.b).

27. The process according to claim 1, wherein the reaction mixture obtained in step iv) is subjected to at least one separation step in order to separate at least partially at least one of the following components:
the at least one transition metal catalyst,
the non-converted at least one alkanol of the formula (III),
the non-converted at least one compound of the formula (II),
reaction products different from the compounds of the formula (I),
the solvent.

28. A process for the production of polyamide 6.6, wherein butadiene is aminated in the process according to claim 23 to obtain 1,6-hexanediamine and wherein the obtained 1,6-hexanediamine is reacted with adipic acid to obtain the polyamide 6.6.

* * * * *